US011565013B2

(12) United States Patent
Murphy et al.

(10) Patent No.: US 11,565,013 B2
(45) Date of Patent: Jan. 31, 2023

(54) SYSTEMS AND METHODS RELATED TO ULTRAVIOLET SANITIZATION

(71) Applicant: PDC Facilities, Inc., Hartland, WI (US)

(72) Inventors: Matthew Murphy, Mukwonago, WI (US); James P. Maslowski, Wauwatosa, WI (US)

(*) Notice: Subject to any disclaimer, the term of this patent is extended or adjusted under 35 U.S.C. 154(b) by 0 days.

(21) Appl. No.: 17/523,586

(22) Filed: Nov. 10, 2021

(65) Prior Publication Data

US 2022/0143240 A1    May 12, 2022

Related U.S. Application Data

(60) Provisional application No. 63/111,926, filed on Nov. 10, 2020.

(51) Int. Cl.
| *A61L 2/10* | (2006.01) |
| *F21V 29/503* | (2015.01) |
| *F21V 5/04* | (2006.01) |
| *F21V 29/70* | (2015.01) |
| *F21Y 115/10* | (2016.01) |

(52) U.S. Cl.
CPC ........ *A61L 2/10* (2013.01); *F21V 5/04* (2013.01); *F21V 29/503* (2015.01); *F21V 29/70* (2015.01); *F21Y 2115/10* (2016.08)

(58) Field of Classification Search
CPC .......... A61L 2/10; F21V 29/503; F21V 29/70; F21V 5/04; F21Y 2115/10
See application file for complete search history.

(56) References Cited

U.S. PATENT DOCUMENTS

| 5,920,075 | A | 7/1999 | Whitehead |
| 6,093,255 | A | 7/2000 | Smith et al. |
| 7,646,199 | B2 | 1/2010 | Dannels et al. |
| 9,662,411 | B2 | 5/2017 | Rizzone |
| 10,478,088 | B2 | 11/2019 | Fink |
| 10,639,387 | B2 | 5/2020 | Bonutti et al. |
| 10,780,189 | B2 | 9/2020 | Randers-Pehrson et al. |
| 10,814,025 | B2 | 10/2020 | Bonutti et al. |
| 2002/0122743 | A1 | 9/2002 | Huang |
| 2014/0230850 | A1 | 8/2014 | Rapoport |
| 2018/0339073 | A1 | 11/2018 | Clynne et al. |
| 2020/0282091 | A1 | 9/2020 | Safraoui |
| 2020/0297879 | A1 | 9/2020 | Bonutti et al. |

(Continued)

FOREIGN PATENT DOCUMENTS

| CN | 201139524 Y | 10/2008 |
| CN | 205832218 U | 12/2016 |

(Continued)

*Primary Examiner* — Andrew J Coughlin
*Assistant Examiner* — Jessica M Apenteng
(74) *Attorney, Agent, or Firm* — Smith Keane LLP

(57) ABSTRACT

A sanitization system includes a plurality of light distribution hubs spaced along a longitudinal frame. Each hub includes a plurality of light emitting modules (e.g., LED chip-on-board) configured to deliver a predetermined type of light (e.g, UVC) to a target surface for a variable or predetermined amount of time at a variable or predetermined intensity to at least partially disinfect and/or sanitize the target surface. The target surface may be an interior surface of a medical imaging device, such as an inwardly facing bore surface and/or patient support surface of an MRI or CT scanner.

6 Claims, 12 Drawing Sheets

(56) References Cited

U.S. PATENT DOCUMENTS

| | | | |
|---|---|---|---|
| 2020/0297880 A1 | 9/2020 | Bonutti et al. | |
| 2020/0306396 A1 | 10/2020 | Bonutti et al. | |
| 2020/0330638 A1 | 10/2020 | Hsu-Luk et al. | |
| 2021/0154345 A1* | 5/2021 | Nolan | H05B 45/10 |
| 2021/0260228 A1* | 8/2021 | Wong | A23L 3/28 |

FOREIGN PATENT DOCUMENTS

| | | |
|---|---|---|
| CN | 206577156 U | 10/2017 |
| CN | 209301786 U | 8/2019 |
| CN | 210358294 U | 4/2020 |
| CN | 210753928 U | 6/2020 |
| CN | 210753998 U | 6/2020 |
| CN | 211243220 U | 8/2020 |

* cited by examiner

SYSTEMS AND METHODS RELATED TO ULTRAVIOLET SANITIZATION

RELATED APPLICATIONS

This application claims the benefit of U.S. Provisional Patent Application Ser. No. 63/111,926, filed 10 Nov. 2020, and entitled "Systems and Methods Related to Ultraviolet Sanitization," which is incorporated herein by reference in its entirety.

BACKGROUND OF THE INVENTION

Medical imaging machines such as magnetic resonance imaging (MRI) machines are widely used as diagnostic tools in medical and healthcare facilities. For example, an MRI is used to non-invasively examine a patients' organs, tissues, and skeletal system by generating high-resolution images of the same. For its broad application and versatility, MRI machines are used to examine many different patients who might suffer from a similarly broad array of illness or ailments.

Like other medical imaging machines, each MRI machine features a large bore, inside of which a patient lies on a movable table. For the duration of the MRI examination (or "MRI scan"), a patient lies still inside the MRI bore. Often, the duration of an MRI examination is between fifteen and ninety minutes.

Because such machines are used to examine a wide variety of sick or healthy patients who suffer or might suffer from any number of illnesses, and because each examination can last a relatively long time, the inside of an imaging bore is prone to become dirty or unsanitary, including receiving and/or harboring bacteria. Another consequence of imaging machines' versatility is that such machines are often used by patients having closely scheduled appointments, leaving little time for medical professionals to sanitize the imaging.

Similarly, the slender imaging bore (i.e. a bore that features a relatively small bore diameter in combination with a relatively long bore length) is cumbersome and difficult for medical professionals or janitorial staff to effectively disinfect or sanitize the interior of the bore, the surface of the patient table, or the various surfaces underneath the table. The difficulty in effectively sanitizing the MRI machine has the potential to magnify the unsanitary conditions inside the imaging bore, which in turn may expose patients to an increased risk of infection. The increased risk of infection is particularly troublesome when the imaging machine is used to examine a patient in an immunocompromised state.

Accordingly, there is a need for a device that can assist in cleaning the inside of an imaging bore. Such a device may include a plurality of ultraviolet (preferably short wave or UV-C) light emitting devices that emit such light onto the surface of the imaging bore, table, and or table support surfaces to quickly and reliably kill surface-borne and airborne microbes, pathogens, and bacteria.

SUMMARY OF THE INVENTION

Generally, embodiments of systems and methods according to the present invention provide improved modalities to sanitize surfaces, including medical imaging machine, patient-contact or patient-facing surfaces, such as bore surfaces in MRI and CT machines. A sanitization device includes a plurality of light emitting hubs spaced along a longitudinal support structure. At least a majority of the physical structure of such device is constructed from preferably non-ferrous materials for use in an electromagnetic field.

Each hub generally includes one or more (preferably 8) light emitting devices, which may include LED chips-on-board housed in a holder (box), which may be formed of mica, and mounted to a heatsink. A lens having preferred transmittance characteristics, such as fused silica, may be held in place by the box and used to cover the LEDs. The light from each light emitting device may have a view angle of greater than 90 degrees, and more preferably about 135 degrees. The light emitting devices preferably emit light of a wavelength of between about 220 nm and about 280 nm (ultraviolet-C or UV-C). The light from each light emitting device preferably overlaps with the light from each radially and longitudinally adjacent light emitting device to blanket a surface to be treated with a predetermined average or minimum light energy density, such as about 20 millijoules per centimeter squared ($mJ/cm^2$) to about 50 $mJ/cm^2$, with about 40 $mJ/cm^2$ more preferable.

According to an aspect of an embodiment of a system according to the present invention, the system includes a power supply (e.g., alternating current, direct current, battery and/or mains) and a longitudinal body member having a body member length along a longitudinal axis. A plurality of hubs are supported by the body member, each hub further including one or more light-emitting devices (e.g., light emitting diode (LED) array, which may be covered by a fused silica lens) that are capable of emitting light radially outwardly from the hubs, the light having a wavelength between about 200 nanometers and about 280 nanometers, with at least about 250 nanometers being preferred.

According to another aspect of an embodiment of a system according to the present invention, the system includes at least three hubs and the hubs are positioned at substantially equal hub intervals along the body member length and between the plurality of hubs. The system more preferably includes five hubs.

According to still another aspect of an embodiment of a system according to the present invention, the light emitted from the hubs forms a substantially cylindrical light envelope along a majority of the body member length, preferably at a predetermined distance from the longitudinal axis.

According to yet another aspect of an embodiment of a system according to the present invention, one or more heatsinks may be operatively coupled to each light-emitting devices.

According to a further aspect of an embodiment of a system according to the present invention, the light emitted radially outwardly from each hub encircles the hub completely at a predetermined distance from the longitudinal axis, such as between about 10 centimeters and about 70 centimeters. Such predetermined distance may be consistent completely around the respective hub, or it may be variable from a first portion of the hub to a different portion of the hub. For example, such predetermined distance from the axis about a top portion of the hub may be greater than the predetermined distance from the axis about an opposite, bottom portion of the hub.

According to an aspect of an embodiment of a method according to the present invention, the method includes a placing step and a first broadcasting step. In the placing step, a plurality of light-emitting devices are placed into a hollow bore defined by an internal bore surface. In the first broadcasting step, light is broadcasted from a first sub-plurality of the light-emitting devices onto a majority of the internal bore surface, the light preferably having a wavelength between about 200 nanometers and about 280 nanometers, with at least about 250 nanometers being preferred. The first broadcasting step may cause the majority of the bore surface to receive a light energy density of about 20 millijoules per centimeter squared (mJ/cm$^2$) to about 50 mJ/cm$^2$.

According to another aspect of an embodiment of a method according to the present invention, the plurality of light-emitting devices have been mounted to a plurality of hubs spaced along a longitudinal body, and the longitudinal body is positioned substantially parallel to a table, the table being translatable into and out of the hollow bore. While the hubs could be placed on the table, they are preferably positioned between the table and the bore surface and spaced from the table, such as by legs supporting the longitudinal body.

According to still another embodiment of a method according to the present invention, the method may further include a second broadcasting step, in which light is broadcasted from a second sub-plurality of light-emitting devices onto a majority of a top surface of the table. The second broadcasting step may cause the majority of the top surface of the table to receive a light energy density of about 20 millijoules per centimeter squared (mJ/cm$^2$) to about 50 mJ/cm$^2$.

According to still another embodiment of a method according to the present invention, the method may further include, as a result of the first and second broadcasting steps, the step of reducing a viable concentration of at least one of microbes, pathogens, and bacteria on the bore surface and on the top surface of the table. The first broadcasting step and the second broadcasting step may be performed at least substantially simultaneously.

DESCRIPTION OF THE PREFERRED EMBODIMENT

Although the disclosure hereof enables those skilled in the art to practice the invention, the embodiments described merely exemplify the invention which may be embodied in other ways. While the preferred embodiment has been described, the details may be changed without departing form the invention, which is defined by the claims.

Figure 1:
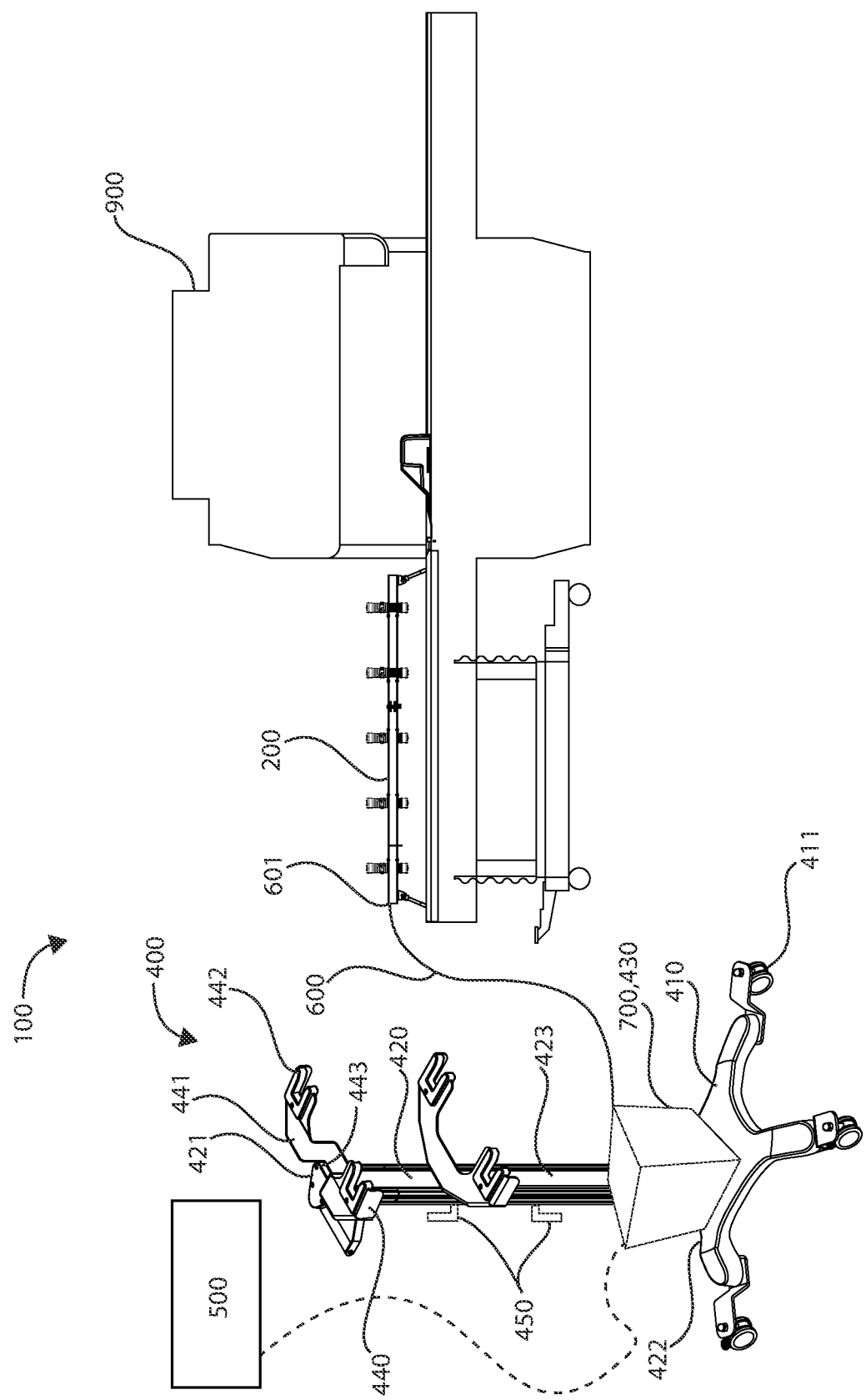
FIG. 1 is a right side elevation view of an embodiment of a sanitization system according to the present invention poised for insertion into a medical imaging device.
Figure 2:
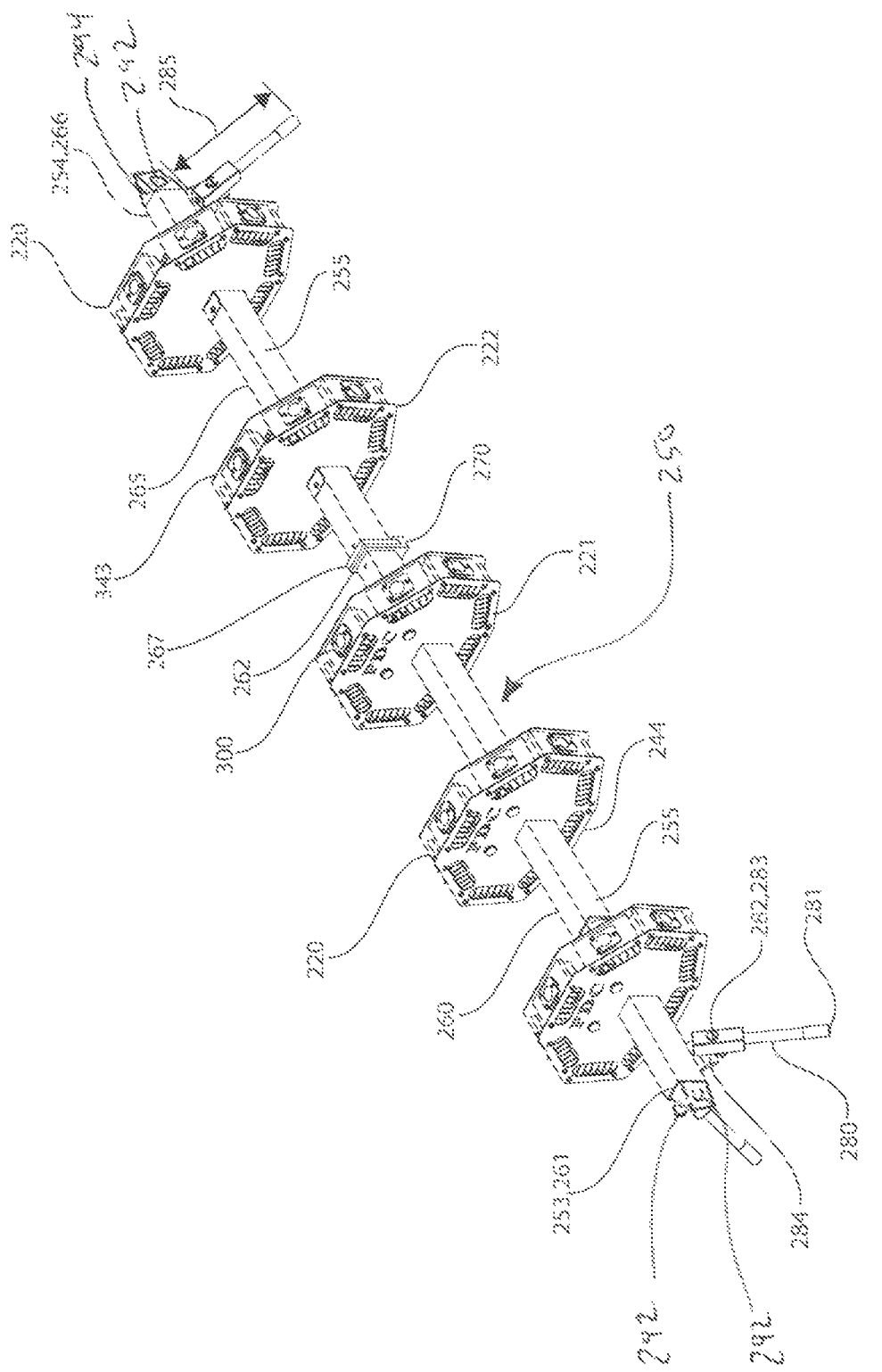
FIG. 2 is a perspective view of a hub system of the sanitization system of FIG. 1.
Figure 3:
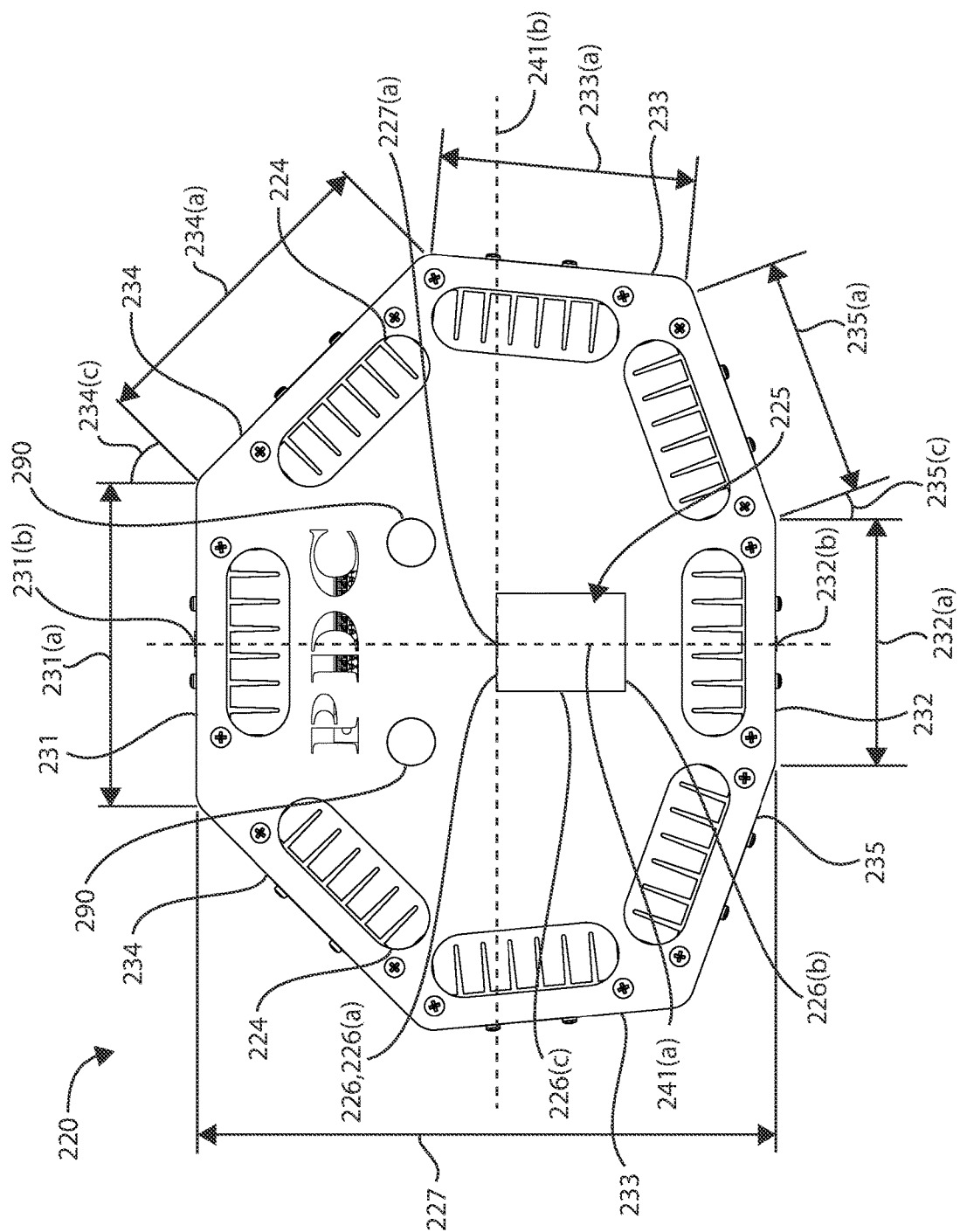
FIG. 3 is front elevation view of a hub of the hub system of FIG. 2.
Figure 4:
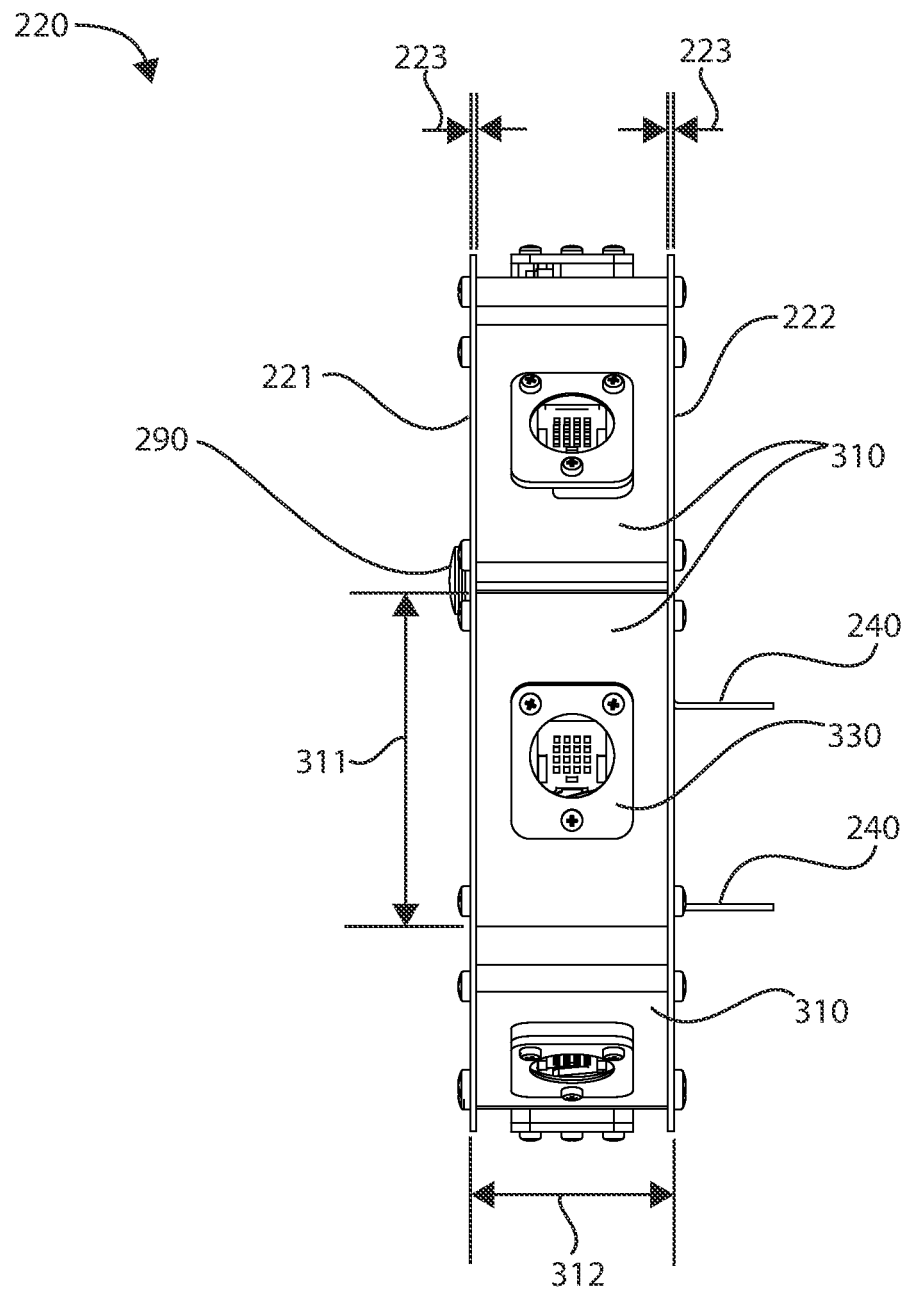
FIG. 4 is a right side elevation view of the hub of FIG. 3.
Figure 5:
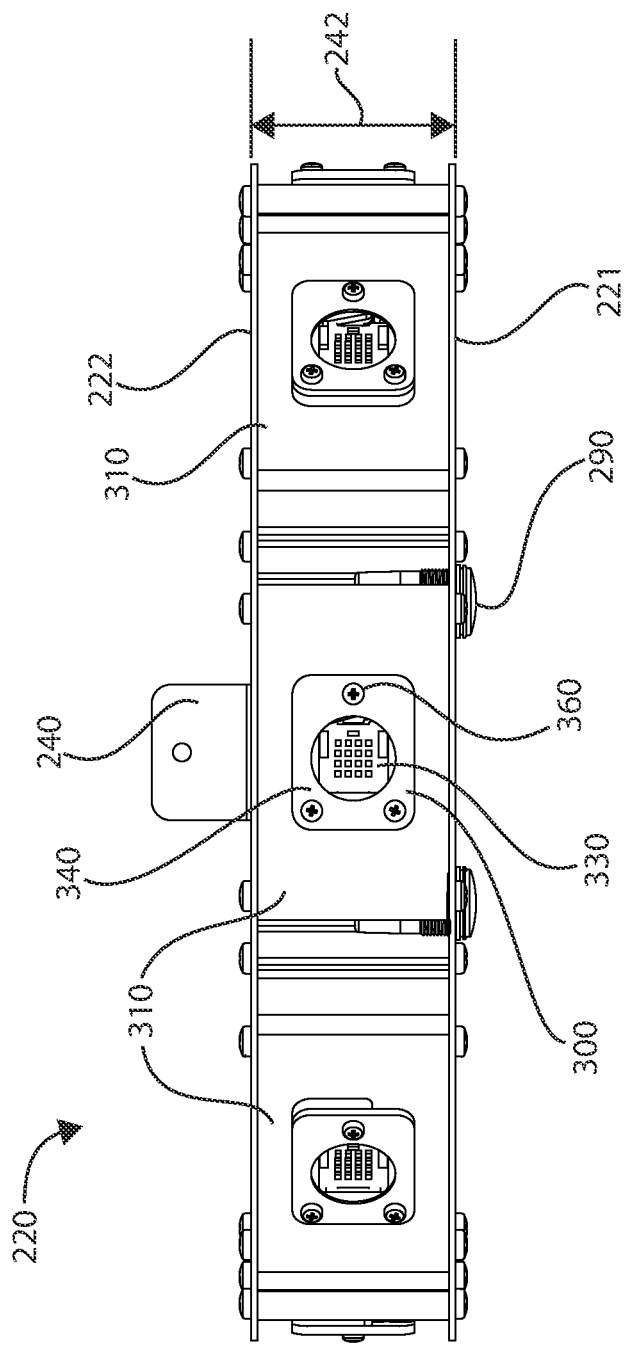
FIG. 5 is a top plan view of a hub of the hub of FIG. 3.
Figure 6:
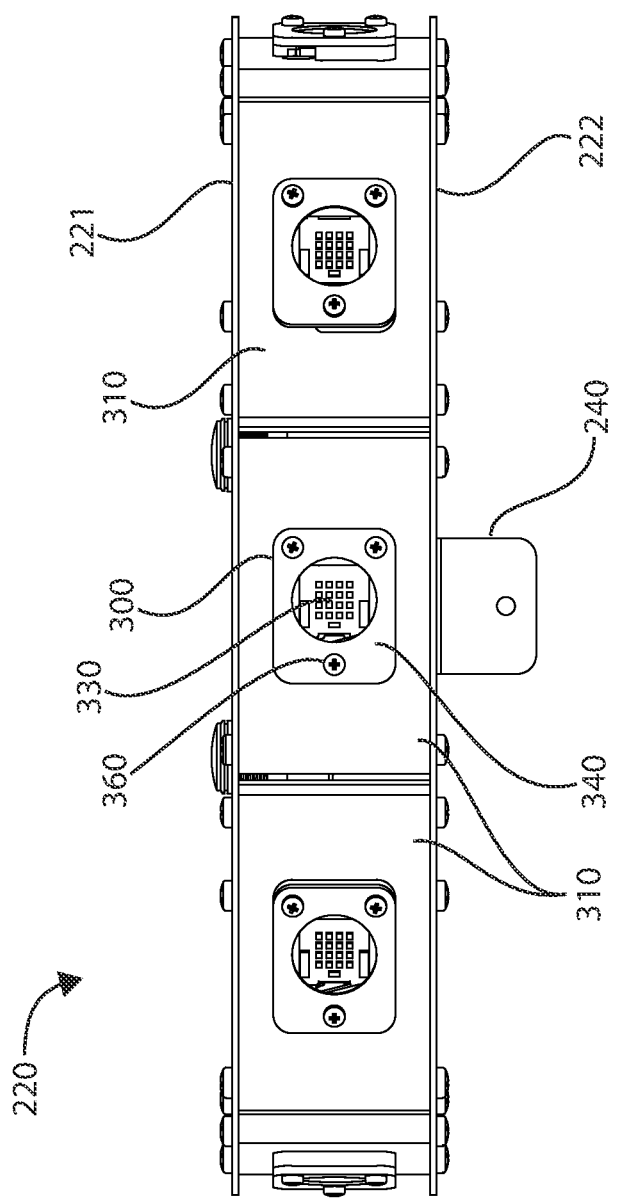
FIG. 6 is a bottom plan view of the hub of FIG. 3.
Figure 7:
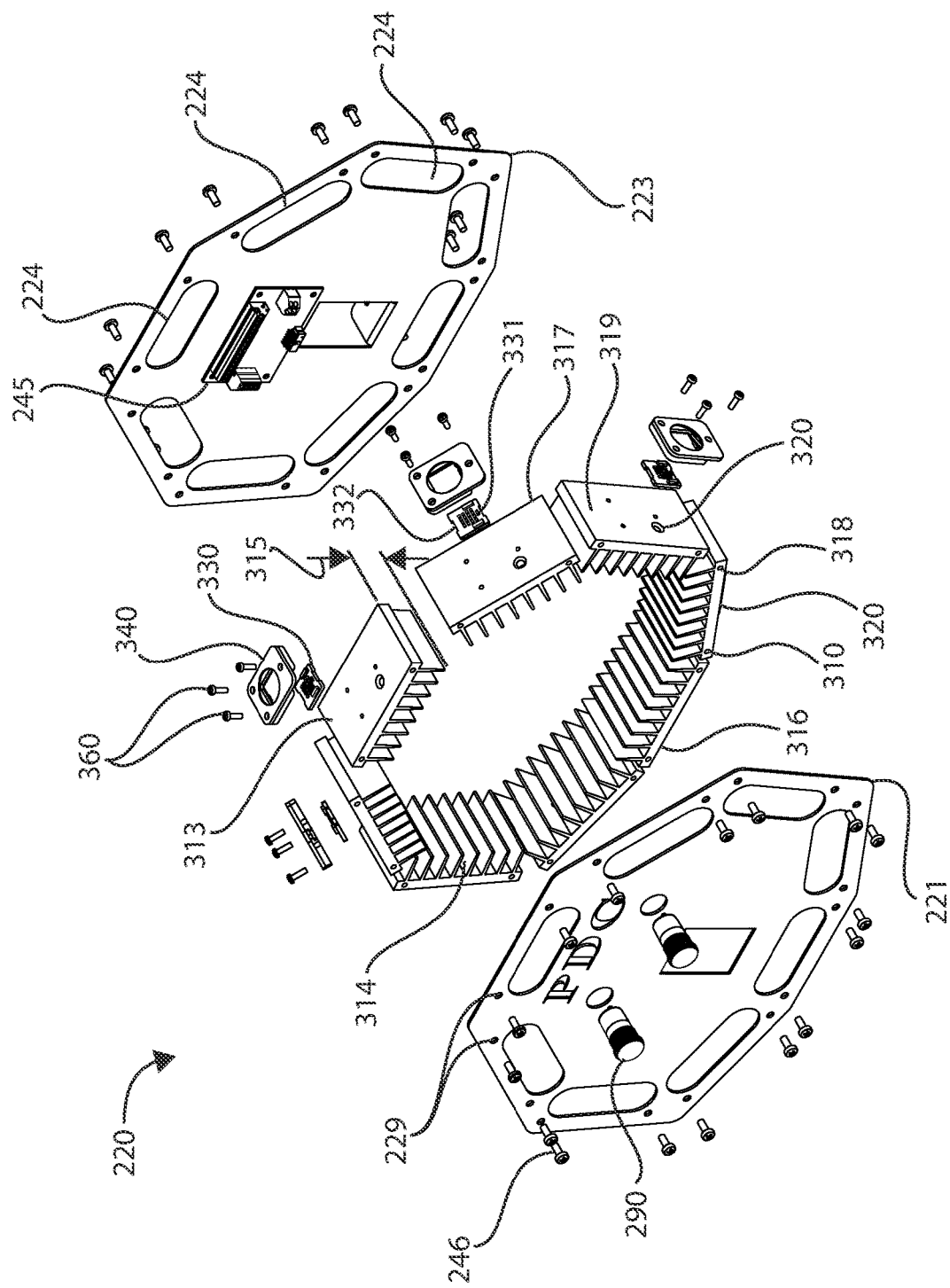
FIG. 7 is an assembly view of the hub of FIG. 3.
Figure 8:
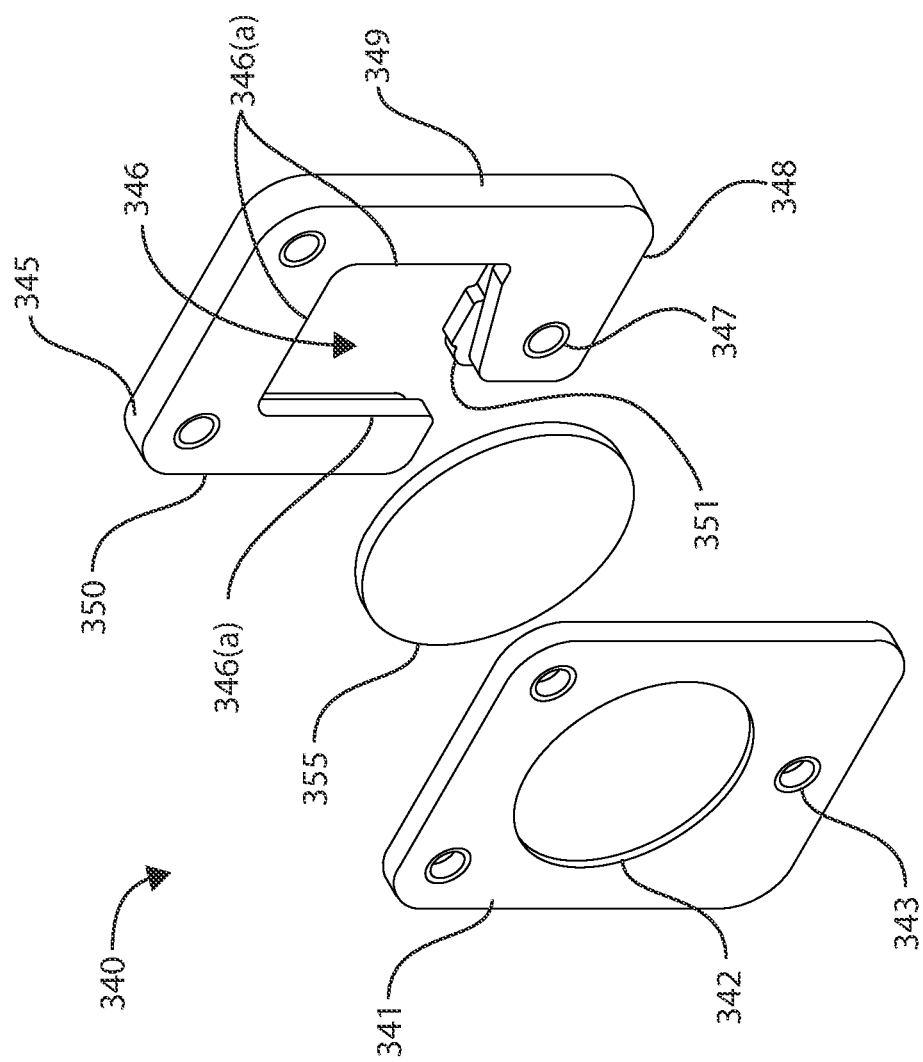
FIG. 8 is a partial assembly view of a box assembly of the hub of FIG. 3.

Turning now to the figures, FIG. 1 shows a sanitization system 100. The sanitization system 100 preferably includes a hub system 200, a control panel 500, a movable cart 400, a power supply 700, and a power cable 600. With reference also to FIG. 2, the hub system 200 preferably includes a plurality of hubs 220 spaced along a longitudinal body 250, a plurality of support legs 280, and one or more indicator lights 290. The control panel 500 or power supply 700 may be located on the cart 400 or separately from the cart. The power supply 700 and controls 500 may be secured (e.g., bolted or adhered) or easily removably coupled (e.g., releasable (such as with hook and loop) or cradled) to the cart 400. In addition, the cart 400 may further provide a storage location of the power cable 600 and hub system 200. The power cable 600 may further be permanently or removably physically and/or electrically coupled to the power supply 700 and hub system 200. Because the hub system 200, controls 500, power supply 700, and power cable 600 are each coupled to or stored on/within the cart 400, the entire sanitization system 100 may be movable via the cart 400, as is described in detail below.

The sanitization system 100 may be used to sanitize a medical imaging machine, such as an MRI machine 900 as depicted in FIG. 1. While the description of the present invention that follows is made with reference to a magnetic resonance (MR) scanner, it should be noted that the present invention may also be used to sanitize other medical imaging equipment, such as computerized tomography (CT) scanners, positron emission tomography (PET) scanners, PET/MR scanners, PET/CT scanners, MR-guided Linac scanners, Nuc Med scanner, or some other imaging bore.

Figure 9:
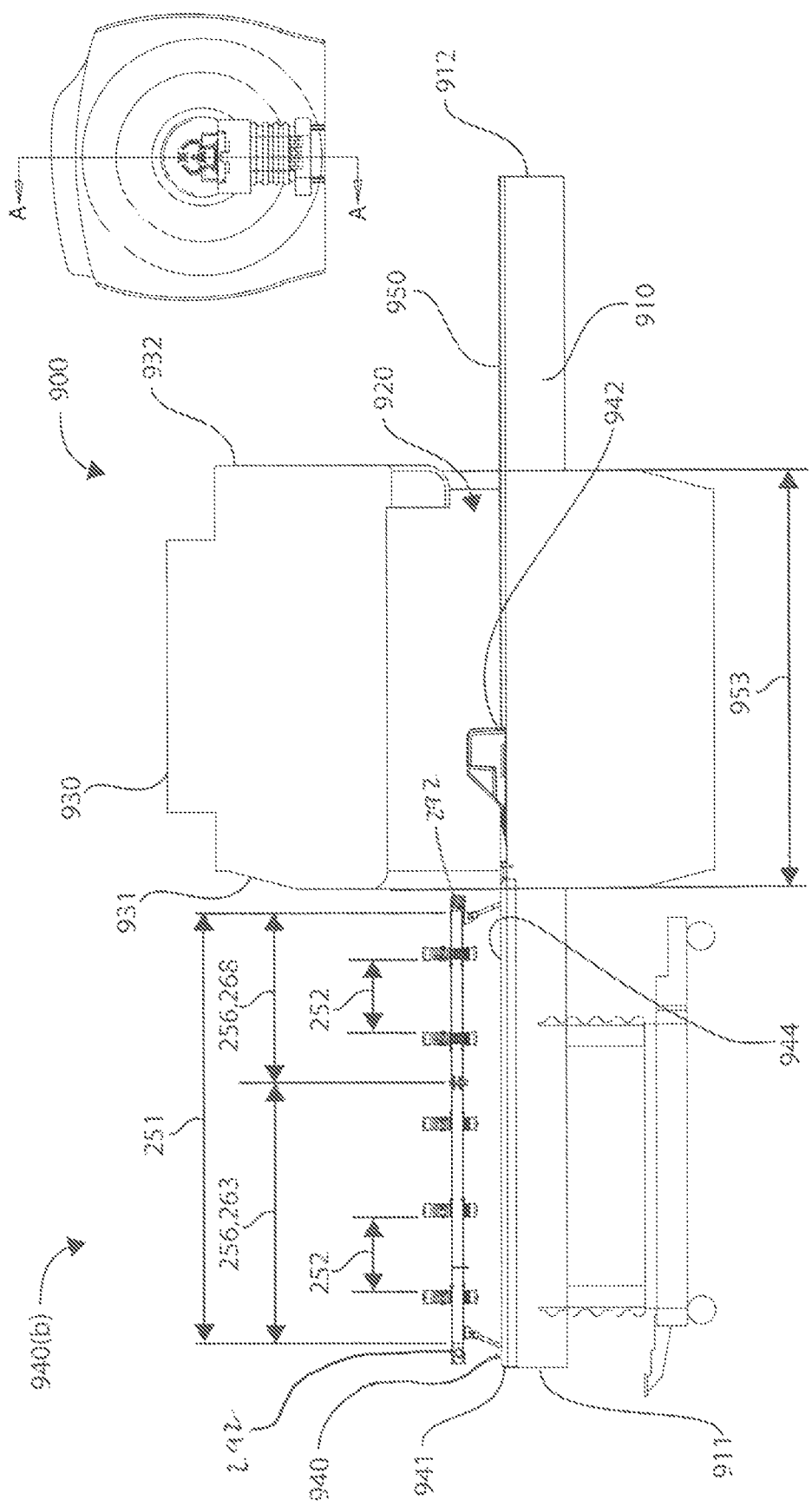
FIG. 9 is a right side elevation view of a hub system in a first position relative to an MRI machine, shown in partial cutaway.

With reference also to FIG. 9, the MRI machine 900 includes an MRI base 910, an MRI bore 920, an MRI scanner body 930, an MRI table 940, and an MRI table track 950. The MRI base 910 has an MRI base front end 911, and an MRI base back end 912. Likewise, the MRI scanner body 930 includes an MRI scanner body front end 931 an MRI scanner body back end 932, and an MRI scanner length 933. The MRI scanner body 930 further includes an MRI scanner body length 933, which is defined by the distance between the MRI scanner body back end 932 and the MRI scanner body front end 931.

The MRI bore 920 has an MRI bore front end 921 an MRI bore back end 922, and an MRI bore diameter 923. The MRI bore 920 extends through the MRI scanner body 930, with the MRI bore front end 921 terminating at the MRI scanner body front end 931 and the MRI bore back end 922 terminating at the MRI scanner body back end 932. The MRI bore 920 also includes an MRI bore surface 924, which is defined by the outer surface of the MRI bore 920 (i.e. the interior surface of the MRI scanner body 930).

The MRI table 940 includes an MRI table front end 941, an MRI table back end 942, and an MRI table top surface 944. The MRI table 940 is slidably mounted along the MRI table track 950. The MRI table track 950 may extend from the MRI base back end 912 to the MRI base front end 911. Accordingly, the MRI table track 950 extends beyond the MRI scanner body front end 931, MRI bore front end 921, MRI scanner body back end 932, and MRI bore back end 922. The MRI table 940 has an MRI table length 943 that is approximately equal to the MRI scanner length 933.

When the MRI machine 900 is in operation, the MRI table 940 is in a scanning position 940(a). In the scanning position, at least a portion of the MRI table 940, and preferably the entire MRI table 940, is disposed within the MRI bore 920. In such orientation, the MRI table back end 942 may be proximate to the MRI scanner body back end 932 and the MRI bore back end 922. Moreover, the MRI table front end 941 may be proximate to the MRI scanner front end 931 and MRI bore front end 921 when the MRI table 940 is in the scanning position 940(a). In other words, when in the scanning position 940(a), the MRI table 940 is preferably substantially disposed within the MRI bore 920.

To the contrary, when the MRI machine 900 is not in operation, the MRI table 940 is in an idle, or loading, position 940(b). In the idle position 940(b), the MRI table 940 extends at least partially outside, and more preferably is not disposed within, the MRI bore 920, but rather the MRI table 940 is disposed between the MRI scanner body front end 931 and the MRI base front end 911. In the idle position 940(b), the MRI table 940 is outside of the bore 920, thus enabling a patient to safely climb on top of the table 940 in preparation for an imaging scan.

The MRI table 940 is further configured to support a patient who is undergoing an MRI examination. Accordingly, a patient will lie on the MRI table 940 when the MRI table 940 is in the idle position 940(b). The MRI table 940 will then be translated along the MRI table track 950 towards the MRI bore 920 and towards the scanning position 940(a). In the scanning position 940(a), the MRI table 940 and the patient will be within the MRI bore 920 (i.e. the MRI scanner body 930 will surround the MRI table 940 and patient). When the MRI table 940 is in the scanning position 940(a), the MRI machine 900 may begin a scanning operation. Throughout this scanning operation, the patient will lay on the MRI table 940 within the MRI bore 920. After the scanning operation is completed, the MRI table 940 will be translated along the MRI table track 950 from the scanning position 940(a) to the idle position 940(b).

During the scanning operation, a patient will lay on the MRI table 940 within the MRI bore 920. The MRI bore diameter 923 must be sufficiently large to accommodate both the MRI table 940 and the patient lying thereon. Preferred or standard MRI bore diameters 923 are approximately 60 to 70 centimeters in diameter.

Because the patient spends a period of time within the MRI bore 920, the MRI bore surface 924 may be exposed to any number of airborne, which may turn surface-borne microbes, pathogens, or bacteria. The MRI table 940 and the MRI table track 950 may similarly be exposed to surface-borne microbes, pathogens, or bacteria. Relatedly, the MRI bore 920 itself (i.e. the area inside the MRI bore 920) may be exposed to airborne microbes, pathogens, or bacteria. Accordingly, the MRI bore surface 924, the MRI table top surface 944, and the MRI bore 920 generally may require sanitization to prevent the spread of disease or illness.

As mentioned above, the sanitization system 100 according to the present invention includes a cart 400, a hub system 200, a power supply 700, a power cable 600, and controls 500. The power supply 700 and controls 500 may be configured to be removably or relatively permanently coupled to the cart 400. Moreover, the hub system 200 and the power cable 600 may be stored on or within the cart 400 when not in use. The power cable 600 may also be coupled to the cart 400 in embodiments where the power cable 600 is removably coupled to the power supply 700, which itself is coupled to the cart 400. Accordingly, the entire sanitization system 100 may be coupled to the cart 400 and can be transported via the cart 400.

The cart 400 may include a base 410, a body 420, a rack 440, and a cabinet 430. The base 410 may further include a plurality of wheels 411, where the wheels 411 are configured as casters, rubberized wheels, etc., and enable the cart 400 to move along a floor surface. The body 420 includes a top 421, bottom 422, front 423, and back 424. The bottom 422 of the body 420 may be coupled to the base 410. The power supply 700 is preferably mounted on the base 410 proximate to the bottom 422. Alternatively, the cart 400 may include an optional cabinet 430 at the base 422 of the cart 400, where the cabinet 430 is configured to house the power supply 700.

The rack 440 and the controls 500 may be located proximate to the top 421 of the body 420. The rack 440 may be configured to receive and/or support the hub system 200 when the hub system 200 is being stored. Specifically, the rack 440 may have one or more arms 441, where said arms include a hanging end 442 and cart end 443. The cart end 443 of the one or more arms 441 is mounted to the cart body 420. The hanging end 442 may be a free end of the one or more arms 441, where the hanging end 442 is configured to support the hub system 200 as it is stored on the cart 400. In some embodiments, the hub system 200 will include one or more body members, as is described in detail below. When comprised in this way, the cart 400 will preferably include at least one arm 441 for each body member. The controls 500 may be mounted on the body 420 of the cart 400 and may further be configured to operate the sanitization system 100, as is described in detail below with reference to FIGS. 9-12.

The cart 400 may optionally include one or more opposing hooks 450 for use in wrapping excess length of the power cable 600. Two hooks 450 may be mounted to the back 424 of the cart body 420, where one hook 450 is proximate to the body top 421, while the other is proximate to the body bottom 422.

Because the sanitization system 100 is configured to be transportable (i.e. moveable from one location to another), the entire sanitization system 100 can be moved to a plurality of locations for use in sanitizing a plurality of imaging machines. For example, one sanitization system 100 can be shared amongst two or more MRI examination rooms by virtue of the transportable nature of the sanitization system 100.

In preferred embodiments, the transportable nature of the cart 400 may permit a user to transport the sanitization system 100 to a location in close proximity to the MRI table 940 of the MRI machine 900 prior to use. This will simplify and streamline the setup procedure of the sanitization system 100. In particular, once the sanitization system 100 has been transported to a location proximate to the MRI table 940, the hub system 200 can be safely and easily configured for use with a decreased risk of injury to the user or damage to the sanitization system 100.

As noted above, the sanitization system 100 is designed to sanitize an imaging bore (such as the MRI bore 920), the MRI table 940, and the MRI table track 950. As described in detail below, the sanitization system 100 is preferably configured to perform a sanitization operation 1100 using a hub system 200 including a plurality of UV-C light emitting devices 300. The hub system 200 may include a plurality of hubs 220 coupled to the hub system body 250. The hub system 200 further includes a plurality of legs 280, which are configured to support the hub system 200 when the hub system 200 rests on a surface, such as the top surface 944 of the MRI table 940.

As noted above, each hub 220 may include a plurality of UV-C light-emitting devices 300. The UV-C light-emitting devices 300 perform a sanitizing function by emitting UV-C light that is capable of killing microbes, pathogens, and bacteria, including the novel coronavirus (COVID-19). The hubs 220 are designed to permit the UV-C light-emitting devices 300 to emit UV-C light radially from the hubs 220 so as to distribute said UV-C light above, below, and to each side of the hubs 220 (i.e. the entire area around the hubs 220). The hub system 200 may include five (5) hubs 220.

The plurality of hubs 220 are spaced along the hub system body 250. The hubs 220 are spaced evenly along the hub system body 250 at intervals equal to a hub spacing length 252. Other embodiments may include a plurality of hubs 220 at irregular intervals where the hub spacing length 252 varies between a plurality of the hubs 220. Moreover, the spacing between hubs 220 along the hub system body 250 may be fixed or moveable. In other words, the hubs 220 may have a variable position along the hub system body 250.

The hub system body 250 may include a body first end 253, a body second end 254, a body length 251 along a longitudinal axis 251a, and a hollow core. The body length 251 is defined as the distance from the first body end 253 to the second body end 254. The hub system body 250 may be configured as a unitary member or a plurality of sub-body members 255. While a unitary hub system body 250 may be used, the hub system body 250 may be comprised of sub-body members 255 temporarily or permanently coupled together via some coupling mechanism (e.g., hinge welded to each sub-body member 255) or joining method (e.g., welding each of the sub-body members 255 together).

In embodiments featuring a plurality of sub-body members 255, each sub-body member 255 may further include a sub-body member length 256. For example, the hub system body 250 may be comprised of two sub-body members 255: a first sub-body member 260 and a second sub-body member 265. The first sub-body member 260 may have a first sub-body member outer end 261, a first sub-body member inner end 262, a first sub-body member length 263, and a first sub-body member cross-section. Likewise, the second sub-body member 265 may have a second sub-body member outer end 266, a second sub-body member inner end 267, a second sub-body length 268, a second sub-body cross-section. In this embodiment, three hubs 220 may be coupled to one sub-body member (e.g., the first sub-body member 260) and two hubs 220 may be coupled to the other sub-body member (e.g., the second sub-body member 265).

When two sub-body members 260, 265 are used, the two sub-body members 260, 265 may be coupled together at a joint 270. In one embodiment, the joint 270 may comprise the second sub-body member inner end 267 interlocking within the first sub-body member inner end 262. In other embodiments, the joint 270 could be created by butting the first sub-body member inner end 262 against the second sub-body member inner end 267 and then coupling the two together using one or more latches or clasps. According to this embodiment, the latches or clasps would prevent the separation of the two sub-body members 260, 265.

In other embodiments, the two inner ends 262, 267 could be coupled together by a hinge. In other words, the joint 270 could be created by a hinge mechanism. More specifically, the first sub-body member inner end 262 could be coupled to the hinge, and the hinge could then be further coupled to the second sub-body member inner end 267. Put another way, the hinge could be coupled between the two inner ends 262, 267. The hinge may be formed as a barrel hinge or some other device allowing the sub-body members 260, 265 to remain attached, yet collapse at least partially for moving and/or storage. The joint 270 may also include a locking mechanism configured to prevent the rotation or de-coupling of the joined sub-body members 260, 265 after they have been coupled.

Alternatively, the hub system body 250 is comprised of three sub-body members 255: a first sub-body member, a second sub body member, and a third sub-body member. The first sub-body member may have a first sub-body first end, a first sub-body second end, a first sub-body length, and a first sub-body cross-section. Likewise, the second sub-body member may have a second sub-body first end, a second sub-body second end, a second sub-body length, a second sub-body cross-section. Finally, the third sub-body member may have a third sub-body first end, a third sub-body second end, a third sub-body length, and a third sub-body cross-section. The first sub-body member and third sub-body member may be substantially similar, with the first sub-body length being approximately equivalent to the third sub-body length and the first sub-body cross-section being substantially similar to the third sub-body cross-section. The second sub-body member, however, may have a smaller second sub-body length than the first sub-body length and third sub-body length.

When the first sub-body member and third sub-body member are at least substantially identical in all material respects (e.g., cross section, length, and etc.), the embodiment featuring three sub-body members may be characterized as having two outer sub-body members and an inner sub-body member, where the inner sub-body member has two mating ends, and each outer sub-body member has a mating end and an outer end. In such embodiments, one mating end of the inner sub-body member is configured to create a joint 270 with the mating end of one outer sub-body member, while the second mating end of the inner sub-body member is configured to create a joint 270 with the mating end of the second outer sub-body member.

The inner sub-body member and outer sub-body members may be coupled together. For example, in the embodiments previously discussed as having three sub-body members, each outer sub-body member may be rotatably coupled to the inner sub-body member via a joint 270. Specifically, a hinge may be removably coupled to the mating end of both outer sub-body members and further removably coupled to the inner sub-body member using one or more fasteners (e.g., nut and bolt, rivets, etc.). Likewise, a hinge may be permanently coupled to the mating end of each outer sub-body members and further permanently coupled to the inner sub-body member via welding or some other operation. In such an embodiment, there are two hinges used to couple the outer sub-body members and the inner sub-body member.

In an exemplary embodiment also featuring three sub-body members, the two hinges may be formed on an inner sub-body member having two mating ends. More specifically, a hinge may be formed on a first inner sub-body mating end and a second inner sub-body second end. According to this embodiment, the outer sub-body member will couple to one hinge, while the other outer sub-body member will couple to the other hinge. Furthermore, in such embodiments, each hinge will rotate about a single hinge axis. The hinge axis may preferably be defined by a sub-body coupling axis about which the adjacent sub-body member (that is, the outer sub-body members) is coupled to the hinge. For example, if an outer sub-body member is coupled to the hinge using a single nut and bolt fastener mechanism having a concentric bolt and nut axis, the bolt and nut axis would be concentric with the hinge axis.

In another embodiment, the hub system body 250 may be comprised of sub-body members 255, including, for example, an inner sub-body member, and two outer sub-body members. The three sub-body members are preferably coupled together using male sub-body connectors and female sub-body connectors. Specifically, the male sub-body connectors are inserted into the female sub-body connectors to couple the sub-body members together. The male sub-body connector and female sub-body connector may be configured as a twist-style connector mechanism, for example. Alternatively, one or more apertures could be formed through both the male sub-body connector and female sub-body connector to permit the insertion of a pin lock or similar locking device to securely couple two sub-body members.

In such embodiments featuring a plurality of sub-body members 255, each sub-body member 255 may preferably include a hollow core. Specifically, each sub-body member 255 may be a hollow, tubular member having a square, circular, rectangular, or other cross-sectional area. Each sub-body member 255 may also be configured differently from other sub-body members 255, such as by having a different sub-body length 263, 268, as is depicted in FIG. 2. Likewise, in embodiments featuring a unitary hub system body 250, the hub system body 250 may be comprised of a hollow tubular member where the cross-section is square, circular, rectangular, or some other shape. Alternatively, the hub system body 200 may be comprised of a solid tubular member where the cross-section is square, circular, rectangular, or some other shape.

Turning now to FIGS. 3-7, an embodiment of a hub 220 according the present invention is shown. As described above, the hubs 220 are coupled to the hub system body 250. Each hub 220 may include a first hub end 221 and a second hub end 222. Each hub may also have a hub thickness 242 and a hub interior, where the hub thickness 242 is defined as the distance from the first hub end 221 to the second hub end 222, and the hub interior is defined as the space between the first hub end 221 and the second hub end 222. The hubs may further include a hub top 243, a hub bottom 244.

To facilitate the coupling of the hubs 220 to the hub system body 250, the hubs 220 include a hub opening 225 having a hub opening cross-section, where the hub opening 225 is formed through both the first hub end 221 and second hub end 222. In other words, the hub opening 225 is a bore that passes through the entire hub 220, spanning the entire hub thickness 242. The hub opening 225 may further include a one or more hub opening edges that define the boundary of the hub opening 225. For example, where the hub opening is rectangular in shape, the hub opening 225 will have four hub opening edges: a top edge 226(a), a bottom edge 226(b) and two side edges 226(c). Contrariwise, if the hub opening 225 is circular in shape, a single and continuous hub opening edge will exist.

The hubs 220 may further include a hub coupling flange 240 on the first hub end 221, second hub end 222, or both the first hub end 221 and second hub end 222. The hub coupling flange 240 may be configured to permit the hub 220 to be fastened to the hub system body 250. The hub coupling flange 240 may be located proximate to the hub opening 225 (i.e. at a hub opening edge). The hub 220 may use two hub coupling flanges 240, both located proximate to the hub opening 225, with one hub coupling flange 240 above the hub opening 225 (i.e. towards the hub proximate to the top edge 226(a)) and another hub coupling flange 240 below the hub opening 225 (i.e. proximate to the bottom edge 226(b)).

To couple the hubs 220 to the hub system body 250, the hub system body 250 may be configured to be accepted by the hub opening 225 (i.e. the cross section of the hub system body 250 is smaller than the hub opening 225). Once the hub system body 250 has been inserted into the hub opening 225 and the hub 220 is positioned at a hub mounting point along the hub system body length 256 (i.e. a position along the length 256 of the hub system body 250 in accordance with the hub spacing length 252), the hub coupling flange 240 may be used to fasten the hub 220 to the hub system body 250. For example, the shank of a fastener (e.g. brass screw) may pass through the hub coupling flange and be fastened into the hub system body 250. In other embodiments, a plurality of fasteners may be used to couple the hub 220 to the hub system body 250 using only one hub coupling flange 240 per hub 220. Alternatively, each hub 220 may be configured to have a plurality of hub coupling flanges 240. In embodiments having a rectangular hub opening cross-section, for example, two hub coupling flanges 240 may be used, with one hub coupling flange 240 at the top edge 226(a) of the hub opening 225, and another hub coupling flange 240 at the bottom edge 226(b) of the hub opening 225.

The first hub end 221 and second hub end 222 are configured as thin, plate-like structures each having a hub end thickness 223. Each hub end 221, 222 may preferably be comprised of a non-ferrous metal material (e.g. aluminum). The first and second hub ends 221, 222 include one or more hub edges. For example, each hub 220 may include a top edge 231, a bottom edge 232, and two side edges 233. The top edge 231 includes a top edge length 231(a) and a center point 231(b). The bottom edge 232 may also include a bottom edge length 232(a) and a center point 232(b). Each of the two side edges 233 may also include a side edge length 233(a). The one or more hub edges together comprise a hub perimeter.

The first and second hub ends 221, 222 may include a perimeter formed by a total of eight edges, namely a top edge 231, bottom edge 232, two side edges 233, two upper diagonal edges 234, and two lower diagonal edges 235. Each of the two upper diagonal edges 234 may include an upper diagonal edge length 234(a), and each of the two lower diagonal edges 235 may include a lower diagonal edge length 235(a). The hub 220 may also include a hub height 227, which is defined by the distance between the top edge 231 and the bottom edge 232 of either the first hub end 221 or the second hub end 222. The hub height 227 may also include a midpoint 227(a).

In such an embodiment, the first and second hub ends 221, 222 are formed as substantially octagonal shapes, symmetric about a centerline 241(a) that extends from the center point 231(b) of the top edge 231 to the center point 232(b) of the bottom edge 232. Likewise, the first hub end 221 and second hub end 222 also include a second centerline 241(b) that is orthogonal to the first centerline 241(a) and extends through the midpoint 227(a) of the hub height 227. However, the first and second hub ends 221, 222 may not symmetrical about the second centerline 241(b). For instance, the first and second hub ends 221, 222 may be generally asymmetrical about the second centerline 241(b).

Each lower diagonal edge 235 extends from a bottom edge 232 at a lower angle 235(c), and each upper diagonal edge 234 extends from a top edge 231 at an upper angle 234(c). The lower angle 235(c) is smaller than the upper angle 234(c). In other words, each lower diagonal edge 235 extends from a bottom edge 232 at an angle closer to parallel to the bottom edge 232 than the upper diagonal edge 234 to the top edge 231.

Each hub 220 may include a plurality of UV-C light emitting devices 300 positioned proximate to the various edges (i.e. proximate to the perimeter of the hub). The UV-C light emitting devices 300 are preferably configured to emit a UV-C light radially from each hub 220 for the purpose of sanitizing surfaces proximate to the hub 220 (e.g. the bore 920 and table 940), as is described in detail below.

Preferably, one UV-C light emitting device 300 may be included for each hub edge. For example, in embodiments featuring first and second hub ends 221, 222 having eight edges (i.e. a top edge 231, a bottom edge 232, two side edges 233, two upper diagonal edges 234, and two lower diagonal edges 235), eight UV-C light emitting devices 300 are disposed around the hub perimeter, one UV-C light emitting device 300 per edge.

Each UV-C light emitting device 300 may further comprise a heatsink 310, a circuit board 330, a box assembly 340, and fasteners 360. Each UV-C light emitting device 300 is configured to emit UV-C light outward from the hub 220 in radial fashion, providing a view angle of about 135 degrees from each device 300. The arrangement of the devices 300 about the hub 220, however, is configured such that emitted UV-C light from adjacent devices 300 preferably at least partially overlaps to provide desired light coverage of a surface to be treated.

The circuit board 330 preferably further includes one or more light emitting diodes (LEDs) 331, preferably disposed in an array, a board body 332, and a wire bundle. The LEDs may preferably be configured to be provided on the board body 332, thus creating a "chip on board" LED, as is a common manufacturing technique for LEDs. The board body 332 may also include a printed electrical circuit used for delivering power to the LEDs for the purpose of emitting UV-C light. The LEDs 331 are selected to emit UV-C light, specifically UV-C light having a wavelength of approximately 220 nm to about 280 nm, with about 250 nm to about 280 nm being preferred, and more preferred about two hundred and seventy-five nanometers (275 nm). However, other embodiments may include LEDs 331 configured to emit light across a broader spectrum of lights, including UV-A, UV-B, infra-red rays. In such embodiments, a plurality of LEDs 331 may be included on the board body 332, where some of the LEDs 331 emit UV-C light, some emit UV-B light, and others emit UV-A light, for example. When light of a variety of wavelengths is used, the board body 332 may require a printed electrical circuit that enables some LEDs to be powered (e.g. only the UV-B LEDs are powered) while other LEDs are not powered.

The box assembly 340 may further include an outer box layer 341, an inner box layer 345, and a lens 355. The outer box layer 341 may further include a lens aperture 342, one or more fastening apertures 343, a height, a width, and a thickness. The outer box layer 341 may preferably be configured to have a generally rectangular shape, although other configurations (e.g. circular, ovular, etc.) may also be used.

The inner box layer 345 may further include a circuit board aperture 346, one or more fastening apertures 347, a top, a bottom 348, a first side 349, and a second side 350, where the top and bottom 348 are substantially parallel and the first side 349 and second side 350 are substantially parallel. The top, bottom 348, first side 349, and second side 350 together form a generally rectangular shape, forming four corners. The first side 349 of the inner box layer 345 may extend from the top of the inner box layer 345 to the bottom 348. Contrariwise, the second side 350 may extend from top of the inner box layer 345 towards the bottom 348 without actually joining the bottom 348. In this way, a void exists where a corner of the inner box layer 345 would be formed if the second side 350 and bottom 348 were joined. The void is preferably configured to provide for the passage of the wire bundle of the circuit board 330.

The outer box layer 341, inner box layer 345, and lens 355 may together be configured to secure the circuit board 330 within the box assembly 340. Specifically, the circuit board 330 may be configured to be sandwiched between the outer box layer 341 and lens 355, and the inner box layer 345. Moreover, the circuit board 330 may be specifically configured to fit within the circuit board aperture 346 of the inner box layer 345. The circuit board aperture 346 may be configured to include a perimeter 346(a), and the perimeter 346(a) may further include a mounting means 351. The mounting means 351 may be configured to secure the circuit board 332 within the box assembly (i.e. to prevent the circuit board 332 from being dislodged from the circuit board aperture 346 of the inner box layer 345. For example, the mounting means 351 may take the form of a small lip or ledge positioned around all or a portion of the perimeter 346(a) of the circuit board aperture 346, where said mounting means 351 supports the circuit board body 332 within the circuit board aperture 346.

Both the outer box layer 341 and the inner box layer 345 may preferably be comprised of a material having heat-resistive properties. Because the LEDS 331 of the circuit board 330 generate heat while activated, it is necessary that the box assembly be made of a material that can withstand high temperatures and retain its dimensions under high-temperature conditions. For that reason, the outer box layer 341 and inner box layer 346 may preferably be comprised of a material such as formica, a ceramic material, or an engineered plastic material.

The lens 355 of the box assembly 340 may include a diameter. The diameter of the lens 355 may be configured to be slightly larger than the diameter of the lens aperture 342. In this configuration, the lens 355 may be sandwiched between the outer box layer 341 and the inner box layer 345 when the two layers are joined. The lens 355 is preferably configured to sit atop the circuit board 330 (which is mounted within the circuit board aperture 346 of the lower box layer 345) such that the LEDs 331 in the circuit board 330 shine through the lens 355. The lens 355 may be comprised of a material having excellent transmittance properties, such as fused silica, for example. Because the lens 355 is mounted over or atop the circuit board 330, the lens 355 may advantageously protect the circuit board 330 and associated LEDs 331 from damage or debris.

The heatsink 310 may include a heatsink base 313, a plurality of fins 314, a heatsink height 315, a heatsink width 311, and a heatsink thickness 312. The heatsink base 313 includes a first end 316 and a second end 317, where the heatsink thickness 312 is defined as the distance between the first end 221 and the second end 222. The heatsink 310 may further include a plurality of heatsink fastening apertures 318, box fastening apertures 319, and a wiring passage 320 formed within the heatsink base 313.

The heatsink fastening apertures 318 may preferably be formed as threaded holes extending only partially into the heatsink body 313. The first hub end 221 and second hub end 222 are preferably fastened to the heatsink 310 via the hub fastening apertures 229 and the heatsink fastening apertures 310 a plurality of hub fasteners 246. Specifically, small fasteners (e.g., brass cap screws, or other preferably nonferrous fasteners) may be inserted through the hub fastening apertures 229 and then threaded into the heatsink fastening apertures 318. In such an arrangement, the each heatsink fastening aperture 318 is configured to substantially align with a hub fastening aperture 229 (i.e. become substantially concentric). For example, if the first end 221 of the heatsink 310 includes two heatsink fastening apertures 318, the first hub end 221 may preferably include two hub fastening apertures 229 at each edge configured to align with the heatsink fastening apertures 318 when the heatsink 310 is mounted proximate to an edge. The heatsink 310 is preferably formed of a non-ferrous material, such as solid aluminum.

The first and second hub ends 221, 222 are preferably fastened to the heatsink 313, as shown in FIGS. 4-7. The first hub end 221 may be mounted to the first end 316 of the heatsink 310 via the hub fastening apertures 229, and the second hub end 222 may be similarly mounted to the second end 317 of the heatsink 310. In this arrangement, the thickness 223 of the first hub end 221 and second hub end 222, and heatsink thickness 312 together comprise the hub thickness 242. In other words, the hub thickness 342 is equal to the sum total of the first and second hub end 221, 222 thicknesses 223 and heatsink thickness 312 when coupled together in the arrangement according to FIGS. 4-7.

The box fastening apertures 319 of the heatsink 310 are positioned on the heatsink body 313 and may preferably be configured to align with the fastening apertures 343, 347 of the outer box layer 341 and inner box layer 345, respectively. Such alignment may permit the box assembly 340 to be fastened directly to the heatsink body 313. Specifically, each of the fastening apertures 343 of the outer box layer 341, the fastening apertures 347 of the inner box layer 345, and the box fastening apertures 319 of the heatsink 310 may be substantially concentric so as to permit the insertion of a fastener 360 through said concentric apertures 319, 343, 347.

The wire passage 320 of the heatsink 310 may be formed as an aperture extending through the heatsink base 313, creating a passageway through which the wire bundle of the circuit board 330 may pass. The wiring passage 320 may be positioned underneath the box assembly 340 when the box assembly 340 is fastened to the heatsink 310. This ensures that the wire bundle protected from damage or debris that may occur during ordinary or extraordinary use.

Each hub 220 may be configured to have eight (8) UV-C light emitting devices 300 (i.e. one UV-C light emitting device 300 per edge). This particular configuration may be advantageous in sanitizing the bore 920 and table 940 because each hub 220 will contribute to an emission of UV-C light around the entire perimeter of the hub 220, thereby sanitizing any object at any radial position around the hub. To further ensure adequate light emittance for sanitization purposes, each circuit board 330 may preferably be capable of emitting UV-C light from the LED 331 with one hundred thirty-five degrees (135°) light output. Put another way, rather than focus the UV-C light in a single spot, the LEDs 331 may preferably be configured to widely distribute UV-C light.

The wide distribution of UV-C light is necessary to assure that UV-C light is emitted between the various hubs 220 of the hub system 200 in order to sanitize an entire bore 920 and table 940. Because each of the hubs 220 are spaced apart at a hub spacing length 252, a portion of the bore 920 and table 940 will not be positioned directly above, around, or below a hub 220. Therefore, it is necessary for UV-C light to be distributed widely so that any portion of the bore 920 and table 940 not directly above, around, or below a hub 220 are also exposed to adequate UV-C light. The wide distribution of UV-C light from each LED 331 as well as the radial placement of a plurality of UV-C light emitting devices 300 around the perimeter of each hub 220 ensures that the an even cylindrical light distribution is created so as to sanitize an entire bore 920 and an entire table 940.

Moreover, the light distribution may be suitable for bores 920 of various diameters, including sixty centimeter (60 cm) and 70 centimeter (70 cm) diameter bores.

The hub 220 may further include a power distribution board 245. The power distribution board 245 may be configured to distribute power to each of the UV-C light emitting devices 300. Specifically, the power supplied to the hub system 200 via the power cable 600 may be distributed to each hub 220, as is described in detail below. The power distribution board 245 may distribute the power delivered to each hub 220 to one or more channels, where each channel is electronically coupled to one or more UV-C light emitting devices 300. For example, the power distribution board 245 may distribute the power delivered to the hub 220 to four channels, where each channel is electronically coupled to two UV-C light emitting devices 300. Each channel could deliver power to and control two adjacent UV-C light emitting devices 300 (e.g., a UV-C light emitting device 300 mounted proximate to the top edge 231 and a UV-C light emitting device 300 mounted proximate to the upper diagonal edge 234), or each channel could operate two nonadjacent UV-C light emitting devices 300 (e.g. UV-C light emitting devices 300 mounted proximate to each side edge 233).

Because the heatsink 310 may preferably be configured to cool the circuit board 330, exemplary embodiments may include a means to air flow to the heatsink fins 314. The first hub end 221 and second hub end 222 may further include a plurality of heatsink openings 224, where said heatsink openings 224 are configured to facilitate air flow to permit the discharge of heat from the hub 220 (specifically from the circuit board 330 and heatsink 310) while the hub 220 is activated (i.e. when the hub 220 is emitting UV-C light). Specifically, the heatsink openings 224 are formed as apertures extending through each of the first hub end 221 and second hub end 221 proximate to the UV-C light emitting devices 300. In other words, each of the heatsink openings 224 provide access to the hub interior. The heatsink openings 224 further allow air to pass through the first hub end 221 and second hub end 222, which may facilitate cooling and temperature regulation of the UV-C light emitting devices 300 during operation.

Both the front hub end 221 and second hub end 222 may include one heatsink opening 224 for each of the UV-C light emitting devices 300 included on each hub 220. For example, in an embodiment including eight UV-C light emitting devices 300, the first hub end 221 includes eight heatsink openings 224 and the second hub end 221 includes eight heatsink openings 224. Furthermore, the heatsink openings 224 on the first hub end 221 may preferably be substantially aligned with the heatsink openings 224 on the second hub end 222. The heatsink openings 224 may be formed as apertures taking a generally circular, pentagonal, rectangular, ovular, or some other shape. To cool the UV-C light emitting devices 300, the heatsink openings 224 may preferably be configured to have a width that is substantially similar to or larger than the heatsink width 311 and a height that is substantially similar to or larger than the heatsink height 315.

The hub system 200 also preferably includes a plurality of legs 280. The legs 280 are configured to support the hub system 200 on top of a surface such as an MRI table 940. The legs 280 may further include a foot end 281, and a coupling end 282. Each leg 280 may be comprised as a slender member, having a leg length.

Besides supporting the hub system 200 as it rests on a surface such as an MRI table 940, the leg length may be specifically configured to provide an optimal distance between the hub 220 (namely the bottom edge 232 of the hub 220) and the MRI table 940 (namely the top surface 944 of the table 940). More specifically, the distance between the top surface 944 of the table 940 and the hub bottom edge 232 is largely dictated by the leg length; a shorter leg length, the closer the hub bottom edge 232 will be to the MRI table top surface 944. Likewise, the shorter the leg length, the farther the hub 220 (namely the hub top edge 231) will be to the bore surface 924 when the hub system 200 is within the bore 920. The respective distance from the hub top edge 231 (or more precisely from light emitting devices 300 disposed proximate thereto) to the bore surface 924 and hub bottom edge 232 (or more precisely from light emitting devices 300 disposed proximate thereto) to the MRI table 944 helps to ensure the UV-C light-emitting devices 300 distribute UV-C light to reach the surface to be treated (e.g., the bore surface 924 and/or table surface 944) at a sufficiently high light energy level (i.e. at least 40 mJ/cm$^2$), as is described below in detail. The leg length is selected to allow the hub(s) 220 to provide adequate light energy to the MRI table surface 944 and the MRI bore surface 924.

The foot ends 281 of the legs 280 may be configured to rest atop the MRI table surface 944 or other surface. In particular, the foot end 281 may comprise a rubberized material or rubberized coating to increase friction between the foot end 281 and the MRI table 940 for the purposes of improving stability thereon. Alternatively, the foot end 281 may be comprised of some other semi-abrasive, roughened, uneven, or knurled material as to increase friction and improve stability. Alternatively, the foot end 281 of the leg 280 may not include any additional material (e.g., rubberized surface), but instead be formed on the end of the leg 280 (i.e. each foot end 281 and its corresponding leg 280 are unitary).

The other end of the leg 280 (i.e. the end opposite the foot end 281) may be a coupling end 282 that is configured to facilitate the coupling of the leg 280 to the hub system 200, specifically to the hub system body 250. For example, the coupling end 282 may be configured to include an aperture 283 through which the shank of a fastener may be inserted for the purposes of fastening the leg 280 to the hub system 200. In preferred embodiments, the leg 280 is rotatably coupled to a leg top 284, where the leg top 284 is further coupled to the hub system body 250. Specifically, the leg top 284 is configured to mount to the hub system body 250, preferably proximate to the first body end 253 or the second body end 254, using fasteners or some permanent mating means. The coupling end 282 of two legs 280 may then be mounted to the leg top 284. In such embodiments, the legs 280 are configured to rotatably mount to the leg top 284 such that the legs 280 can pivot around an axis formed through the coupling end aperture 283. This arrangement is advantageous because the legs 280 may be rotated into an outward position to support the hub system 200, or the legs 280 may be rotated inwards for the purpose of storing the hub system 200 when it is not in use.

The legs 280 may be coupled to the first body end 253 and second body end 254 of the hub system body 250 in embodiments featuring a unitary hub system body 250. Alternatively, the legs 280 may be coupled to one or both ends of one or more sub-body members 255 in embodiments featuring a hub system body 250 comprised of a plurality of sub-body members 255. In preferred embodiments featuring two sub-body members 260, 261, the legs 280 may be coupled only to the outer end 261 of the first sub-body member 260 and to the outer end 266 of the second sub-body member 265.

In an alternative embodiment, the legs 280 are not fastened or mated to the hub system 200 or hub system body 250 at all. Instead, a two or more legs 280 might be formed together on a leg stand to support the hub system body 250, where the stand includes two or more legs and a leg stand top. The top may be configured to provide a surface upon which the hub system body may rest. Accordingly, the top may be a substantially horizontal, planar surface in embodiments where the hub system body 250 has a bottom that is also substantially horizontal and planar (e.g., in embodiments where the hub system body 250 has a rectangular cross-section). Alternatively, the top be take a concave or semi-circular shape in embodiments where the hub system body 250 has a bottom that is substantially round (e.g., in embodiments where the hub system body 250 has a circular or ovular cross-section).

In other embodiments, a sub-body member 255 may be coupled to the hub system body 250 in such a way as to avoid the need for any legs 280 to support said sub-body member 255. For example, the hub system 200 may include seven hubs, where five hubs 220 are arranged as is depicted in FIGS. 1-2 (i.e. with three hubs coupled to the first sub-body member 260 and two hubs 220 coupled to the second sub-body member 265) and two hubs 220 are coupled to a separate auxiliary sub-body member. The auxiliary sub-body member may be configured to hang over the back end 942 of the table 940 such that the hubs 220 mounted to the auxiliary sub-body member are hanging over the table track 950. In this embodiment, the hubs 220 of the auxiliary sub-body member may be configured to sanitize the table track 950, rather than the table top surface 944. Because the auxiliary sub-body member is hanging over the back end 942 of the table 940, legs 280 resting on the table top 940 cannot be disposed underneath the auxiliary sub-body member. Therefore, auxiliary sub-body members as described herein may need to be supported without the use of legs 280, perhaps by using a joint 270 having a plurality of locking mechanisms to prevent rotation of the auxiliary sub-body member.

One or more of the hub(s) 220 may also include one or more indicator lights 290. The indicator lights 290 may be mounted to the first end 221, second end 222, or both ends 221, 222 of the hubs 220. The indicator lights 290 are preferably mounted such that the light emitted from the indicator lights 290 is visible from outside of the hubs 220 (rather than emitting light into the interior of the hubs 220). In preferred embodiments, each hub 220 of the hub system 200 may include one or more indicator lights. In other embodiments, indicator lights 290 may be mounted to only one or two hubs 220 of the hub system, such as one hub 220 of each sub-body member 255, for example.

The indicator lights 290 may be included on each of the hubs 220 or fewer than each of the hubs 220. For example, the hub 220 in closest proximity to the first end 253 of the hub system body 250 may include indicator lights 290 as well as the hub 220 in closest proximity to the second end 254 of the hub system body 250. The indicator lights 290 may be visible by a person who is able to view the MRI bore front end 921 and MRI bore back end 922.

The indicator lights 290 may be light emitting diodes (LED) or some other light-emitting device capable of displaying one or more visible colors. In one embodiment, the indicator lights 290 may be LEDs capable of displaying a plurality of colors, including, for example, red, green, and orange. In other embodiments, the indicator lights 290 may include a plurality of LEDs, each capable of displaying one or more colors. The operation of the indicator lights 290, specifically the display of one or more colors or the blinking, pulsing, intermittent, or constant display of colored light may communicate information to users and other persons near the sanitization system 100.

In order to perform a sanitization operation 1100 (i.e. emit UV-C light from the UV-C light-emitting devices 300 of the hubs 220 to sanitize an imaging bore 920 and the associated table 940 as described in detail below), it is necessary to provide power to the hub system 200. This may be achieved by electrically coupling a power cable 600 having one or more connecting ends 601 to the hub system 200, where the power cable 600 is further coupled to the power supply 700. The power cable 600 has one connecting end 601 and may be coupled to the hub system 200 at a power coupling point. The power coupling point may be located at one end (i.e. the first body end 653 or second body end 654) of hub system body 250, or the coupling point could be located at some other point along the body length 251 of the hub system body 250. However, the power cable 600 may also be coupled to the hub system 200 at some other location, such as to one or more of the hubs 220 which may be further coupled to the hub system body 250.

The power cable 600 may be coupled to the hub system 200 at only one power coupling point. In these embodiments, power is further distributed to each of the hubs 220 from the power coupling point via connector cables mounted on or within the hub system body 250. The connector cables may preferably be mounted within a hub system body 250 or plurality of sub-body members 255, each having a tubular structure and a hollow core. The connector cables may further couple to each hub 220 though the hub system body 250 by, for example, a wiring aperture proximate to a hub mounting point. The wiring aperture is preferably located between the first hub end 221 and second hub end 222 after the hub 220 is coupled to the hub system body 250. In such an embodiment, each of the connector cables would be mounted within the hollow core of the hub system body 250 and couple to each hub 220 within the hub interior, specifically to the power distribution board 245. This arrangement may protect the connector cables from damage or misuse.

In other embodiments, the power cable 600 includes a plurality of connecting ends 601 that are configured to couple to a plurality of power coupling points. For example, the plurality of connecting ends 601 may each couple a power coupling point, where one power coupling point is located at each hub 220. In such embodiments, the connecting ends 601 each branch from a single power cable 600. The single power cable 600 is then coupled to the power supply 700 at a single point. In other words, preferred embodiments may not include multiple power cables 600, each comprising one connecting end 601 to couple to one of the plurality of power coupling points.

According to an exemplary embodiment that includes a first sub-body member 260 and a second sub-body member 265, the power cable 600 may be connected to a single power coupling point located on only one of the sub-body members 260, 265. In this embodiment, power may be further provided to each of the remaining sub-body members 265, 260 via one or more jumper cables that electrically couple the remaining sub-body members 265, 260 to the other sub-body member 260, 265 that includes the power coupling point.

For example, the power coupling point may be located on the first sub-body member 260, where the first sub-body member 260 has an outer end 261 and an inner end 262. The power coupling point may be located proximate to the outer end 261. A jumper terminal may be provided proximate to the inner end 262 of the first sub-body member 260. The power coupling point may further be electrically coupled to the jumper terminal. The second sub-body member 265 having an outer end 266 and an inner end 267 may include a jumper terminal at the inner end 267. The first sub-body member 260 is then electrically coupled to the second sub-body member 265 by coupling the respective jumper terminals with a jumper cable. The jumper terminals of the second sub-body member 265 may be electronically coupled to connector cables mounted within the hollow core of the second sub-body member 265 and further coupled to each of the hubs 220 mounted to said sub-body member 265.

Furthermore, continuing with the example above, the second sub-body member 265 may include a second jumper terminals located proximate to the outer end 266. This second jumper terminal may then be electrically coupled to an auxiliary sub-body member in embodiments having an auxiliary sub-body member.

The jumper terminals may include an electrical post, where the post is capable of accepting an alligator-clip style electrical connector. Alternatively, the jumper terminal may include the female or male end of an electrical connector (e.g., molex, ethernet, etc.). In this embodiment, the jumper terminal is capable of accepting the corresponding male or female end of an electrical connector in order to establish an electrical connection.

Instead of jumper cables and jumper terminals, the electrical connection can be established between the various sub-body members 255 by combining electronic coupling means within the mechanical coupling means, such as by including a male electrical pin connector disposed on or within the male sub-body connector and configured to mate with a female electrical pin connector disposed on or within the female sub-body connector, for example. Other male and female electrical connectors may also be used (e.g., molex, JST, or IEC connectors). In such embodiments, an electrical connection is established when the sub-body members 255 are coupled (i.e. when the male sub-body connector is inserted into the female sub-body connector).

In any of the above-described configurations or an alternative configuration, the power provided to each sub-body member 255 may preferably be configured to provide power to each of the hubs 220 for at least the purpose of emitting UV-C light from each hub 220.

Rather than providing power to the hub system 100 via a power cable 600 coupled to an external power supply 700 and a power connection point on the hub system 200, the requisite power for the hub system 200 may be provided by a battery or some other on-board power supply method. In such embodiments, each hub 220 may have its own battery or power supply mechanism or the entire hub system 200 may be powered via a single battery or power supply mechanism.

The power supply 700 may be a direct current power supply including a plug that is compatible with a standard 120-volt wall outlet. Similarly, the power cable 600 is coupled to the power supply 700. In preferred embodiments, the power supply may deliver power through the power cable 600 to the hub system 200 and control panel 500. The control panel 500 may also command the power supply 700 to send power to the hub system 200. Likewise, the control panel 500 may monitor the power sent from the power supply 700 to the hub system 200 in order to ensure a sufficient amount of power is delivered to the hubs 220. The power supply 700 may also include security means, such as a lock-out key mechanism, that may prevent the unauthorized use of the sanitization system 100. Additionally, the power supply 700 may be stored in a cabinet 430 that is mounted to the cart 400, where the cabinet 430 may house the power supply 700 while protecting the power supply 700 (and users or bystanders) from harm. The power supply 700 may be a rechargeable power supply (e.g., battery), and/or may include an inverter or converter, as required, which may receive power from a power mains.

The sanitization system 100 is designed to kill microbes, pathogens, and bacteria on medical equipment using a plurality of hubs 220 that emit UV-C light at a sufficiently high energy level and with sufficient light distribution. The sanitization system 100 may be particularly useful in sanitizing the bore 920 and table 940 of the MRI machine 900 depicted in FIG. 1. However, the sanitization system 100 may also be useful in sanitizing other medical equipment, such as a CT scanner, PET scanner, PET/MR scanner, PET/CT scanner, MR-guided Linac, Nuc Med, or other imaging bore.

Figure 12:
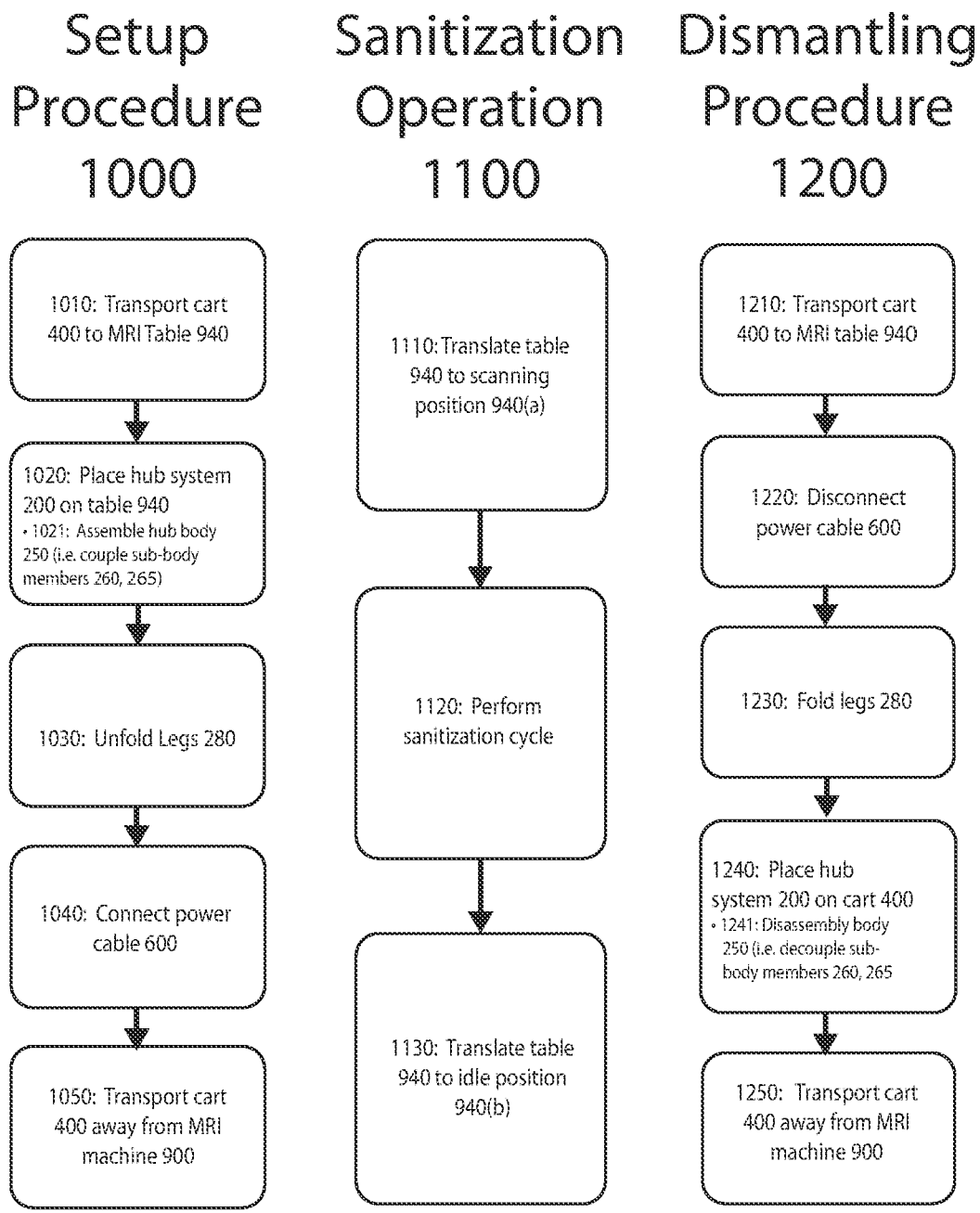
FIG. 12 is a block diagram of an embodiment of an operating procedure for a sanitization system according to the present invention.

Referring now to FIG. 12, an operational flow chart of the sanitization system 100 is shown. When used to sanitize an MRI machine 900, the sanitization system 100 must first be configured (i.e. set up) for use on the MRI machine 900, according to a setup procedure 1000, or be pre-configured. Once the sanitization system 100 has been configured, a sanitization operation 1100 may be performed. After the sanitization operation 1100 is complete, the sanitization system 100 must be dismantled and stored for future use, according to a dismantling step 1200.

Before the sanitization system 100 can be used to kill microbes, pathogens, and bacteria on medical equipment, the sanitization system 100 must first be configured for use according to a setup operation 1000. Setup of the sanitization system 100 for use generally requires the setup of the hub system 200 on the MRI table 940 of the MRI machine 900 and coupling the power cable 600 to the hub system 200 and power supply 700.

To prepare the sanitization system 100 for use, the hub system 200 must be placed on the MRI table 940. Because the sanitization system 100, namely on or with the cart 400, is configured to be portable, the setup operation 1000 may require a first step 1010 of transporting the sanitization system 100 via the cart 400 to a location in close proximity to the MRI table 940.

Once the cart 400 is proximate to the MRI table 940 according to the first step 1010, the setup process 1000 may require a second step 1020 of removing the hub system 200 from the cart 400 and placing it on the MRI table 940. Depending on whether a unitary hub system body 250 is used, or whether a hub system body 250 comprised of a plurality of sub-body members 255, an optional hub system body assembly sub-step 1021 may be used. In embodiments utilizing a plurality of sub-body members 255, the hub system 200 will need to be assembled before it can be set on the MRI table 940 for the sanitization operation 100.

The assembly sub-step 1021 may include coupling the sub-body members 255 together. The requisite procedure for coupling the various sub-body members 255 depends on the joint used to join the sub-body members (e.g., pin lock system, quick connect coupling, hinge and latch, etc.). For example, in an embodiment featuring male sub-body connectors and female sub-body connectors, the coupling of the sub-body members 255 may include insertion of the male sub-body connectors into the female sub-body connectors and locking the members together via pin lock or some other locking mechanism. In embodiments using a hinge to couple sub-body members 255, the various sub-body members 255 may already be coupled together, but are stored in a folded position. Coupling is thus not necessary in such embodiments, but it may be necessary for the user to unfold the hub-system body 250 at each of the hinges. It may further be necessary for the user to lock the hinges in an open (i.e. unfolded) position.

After the hub system body 250 assembly procedure according to the second step 1020 is complete, a third step 1030 of securing the legs 280 must be performed. Securing the legs 280 in a standing position may also vary depending on the arrangement of the legs 280. The legs 280 may be rotatably mounted on the outer ends 261, 266 of the first and second sub-body members 260, 265. In such embodiments, the legs 280 may be stored in a folded position substantially parallel to the hub system body length 251. Accordingly, the legs 280 may need to be rotated about the coupling aperture 283 so that the legs 280 may extend downward from the hub system body 250 towards the table 940.

Once steps one through three 1010, 1020, 1030 are completed, the user may next perform a fourth step 1040 of establishing an electrical connection. This step may be accomplished by first coupling the power cable 600 to the power supply 700. The power cable 600 is permanently connected to the power supply 700 (i.e. the power cable 600 is hardwired to the power supply 700) or the power cable 600 may be coupled to the power supply 700 via an IEC pin connector or similar electrical connector (e.g., molex, JST, etc.).

Similarly, the power cable 600 must also be electrically coupled to the hub system 200. The power cable 600 can be coupled to the hub system 200 by coupling the connecting end(s) 601 of the power cable 600 to the power coupling point(s) located on the hub system body 250 (e.g., at the first end 253 or second end 254 of the hub system body 250 or at some other position along the hub system body length 251). The power cable 600 may include the male or female end of an IEC pin connector or similar electrical connector, while power coupling point may include the female or male end of an IEC pin connector or similar electrical connector, respectively. Moreover, in embodiments featuring a plurality of sub-body members 255, the fourth step 1040 may include connecting jumper cables to jumper terminals, as described above. The hubs 220 may include an indicator light 290 configured to indicate that power is being delivered to the hub system 200 after the power cable 600 has been coupled according to the fourth step 1140.

Finally, the user may perform a fifth step 1050 of moving the cart 400 from a position in close proximity to the table 940 to a safe distance from the MRI machine 900. For example, a user may transport the cart 400 to an adjacent room or to an opposite end of the MRI room so that the hub system 200 can be activated while the operator and any bystanders are away from the hubs 220 in order to avoid potentially harmful exposure to UV-C light. Accordingly, it may be necessary for the power cable 600 to be of a sufficiently long length so as to enable the cart 400 to be moved to a safe distance (e.g. 10-100 feet) from the MRI machine 900 while still permitting the power supply 700 to be coupled to the hub system 200 via the power cable 600.

After the hub system 200 has the setup operation 1000 has been completed, a sanitization operation 1100 may be performed. The sanitization operation 1100 may include a first step 1110 of translating the table 940 from the idle position 940(*b*) to the scanning position 940(*a*). Once the table 940 is in the scanning position 940(*a*), the hub system 200 will be located within the bore 920 and will thus be prepared to sanitize the table top surface 944 and bore surface 924.

The sanitization operation 1100 may then include a second step of initiating a sanitization cycle 1120, which will ultimately lead to the activation of hubs 220. Once the hubs 220 are activated, the hubs 220 will emit UV-C light and kill microbes, pathogens, and bacteria.

Said initiation of a sanitization cycle 1120 can be performed through use of the controls 500, which are preferably mounted on the cart 400. The controls 500 may be configured to command the power supply 700 to send power via the power cable 600 to the hub system 200 for the purposes of activating the hubs 220. Once activated, the hubs 220 may be configured to emit UV-C light during the sanitization cycle 1120. The sanitization cycle 1120 may include the continuous activation of the hubs 220 for a pre-determined period of time in order to effectively kill all microbes, pathogens, and bacteria. The duration of the sanitization cycle 1120 may be between five and seven minutes when the UV-C light emitting devices 300 provide UV-C light at an energy level of 40 mJ/cm$^2$ to the surface to be treated. Alternatively, a user may select from a variety of preset sanitization cycle durations, such as a deep clean cycle, or a cycle designed to sanitize a different machine (e.g., a computerized tomography (CT) scan machine). In another embodiment, the sanitization cycle 1120 may be predetermined based on some input value, such as (a) the type of imaging scan performed by medical professionals (e.g., a full body MRI scan or a partial body MRI scan), (b) the duration of the imaging scan performed buy medical professionals, (c) the health of a patient recently scanned or to be scanned subsequently, (d) the desired energy level of the UV-C light emitted onto the bore surface 924 and table top surface 944 (e.g. 40 mJ/cm$^2$, 50 mJ/cm$^2$, etc.), or (e) some other value selected by medical professionals.

The sanitization cycle 1120 may be manually controlled by a user via the controls 500. For example, the user may command the activation of the hubs 220 via a switch (e.g. toggle switch or two-way switch). The hubs 220 may be configured to remain activated so long as the switch is in an "ON" position. To deactivate the hubs 220 (i.e. to command the hubs 220 to stop emitting UV-C light) in such an embodiment, the user may be required to move the switch to an "OFF" position. Alternatively, the sanitization cycle 1120 may be configured according to various programs. For example, the controls 50 may be configured to command one or more preset sanitization cycles 1120 according to various programs, such as a standard sanitization cycle, a shortened sanitization cycle, an extended sanitization cycle, a table-only sanitization cycle a bore-only sanitization cycle, or some other cycle. In this embodiment, the sanitization cycle 1120 may begin when a user selects a program using the controls 500. The sanitization cycle 1120 may then begin and continue for some pre-determined duration according to the selected program. Once the sanitization cycle 1120 has run its course, the controls 500 may automatically command the deactivation of the hubs 220. The automated nature of this control method permits a user to passively operate the hub system 200 by simply starting the sanitization cycle 1120 without requiring the user's presence for the duration of the sanitization cycle 1120.

Alternatively, with or without the user's selection of a sanitization cycle 1120, the hubs 220 may automatically activate (or prevent activation) in response to feedback provided by one or more proximity or motion sensors 292 (such as an infrared motion detector) which may be positioned on one or more hubs 220 or at one or both ends of 253, 254 of the body 250. As shown, a preferred mounting location for sensors 292 is on opposing sides of a triangular prism-shaped cap 294 on one or each end 253, 254 of the body 250. The sensors 292 may be configured to sense the presence of the hub system 200, or an individual hub 220 within the bore 920, or the presence of motion within a predetermined distance from the sensor 292 or motion within a room in which the device 200 is placed. In such an embodiment, the proximity sensors 292 operate as a safety mechanism to prevent the activation of the hubs 220 and the associated emittance of UV-C light when the hub system 200 is entirely or partially outside of a bore 920 and/or when there are humans near the device or within the room in which the device 200 is situated. This in turn minimizes risk that any persons will be exposed to UV-C light.

In embodiments using proximity sensors 292 on one or more, or each, hub 220, the hubs 220 may be configured to activate individually as each hub 220 passes into the MRI bore 920. Specifically, as the table 940 is translated into the bore 920, each hub 220 may be configured to activate once the proximity sensors 292 on the individual hub 220 sense that the individual hub 220 is within the bore 920. Other hubs 220 that are not yet within the bore 920 may remain deactivated until they are present within the bore 920.

Likewise, the proximity sensors 292 may also be configured to deactivate the hubs 220 when the proximity sensors 292 detect that the hub or hubs 220 are no longer within the bore 920. This ensures that if the table 940 is translated back out of the bore 920 during the sanitization operation 1120, the hubs 220 will deactivate so as to ensure that UV-C light is not emitted in the presence of the user or other persons. When proximity sensors 292 operate in this way, the hubs 220 may only be permitted to operate when the hub or hubs 220 are within the bore 920, thus preventing the hub system 200 from being used in a harmful or dangerous manner.

The proximity sensors 292 may also be configured to detect the presence of a person in close proximity to the hub system 200 during the sanitization cycle 1120. Specifically, if the proximity sensors 292 detect that a person is approaching the hub system 200 while it is sanitizing a bore 920, the hubs 220 may deactivate before the person becomes too close to the hub system 200 (e.g., within ten feet of the hub system 200). In the same way, the proximity sensors 292 may detect the presence of persons before the hubs 220 are activated but after the hub system 200 is connected to the power supply 700. For example, after a user couples the power cable 600 to the hub system 200 (i.e. after power is provided to the hub system 200), the proximity sensors 292 may automatically operate to detect the presence of one or more persons nearby. In this embodiment, the presence of at least one person nearby may prevent the activation of the hubs 220.

Because proximity sensors 292 may be used to command or prevent the activation of the one or more hubs 220, it is alternatively possible to perform the first step 1110 of the sanitization operation 1100 (i.e. translating the table 940 from the idle position 940(*b*) into the scanning position 940(*b*)) after initiating a sanitization cycle 1120. More specifically, a selected sanitization cycle 1120 may be configured to command the activation of the hubs 220 after the proximity sensors 292 detect the presence of the hub or hubs 220 within the bore 920. Accordingly, the sanitization cycle 1120 can be initiated before the table 940 is translated into the scanning position 940(*a*) according to the first step 1110 of the sanitization operation 1100. However, according to such a sanitization cycle 1120, the actual sanitization of the bore 920 (i.e. the use of UV-C light to kill microbes, pathogens, and bacteria) will not occur unless the table 940 is subsequently translated into the bore 920.

During the sanitization operation 1100 (including before or after the sanitization cycle 1120), the hub system 200 may visually communicate information via the one or more indicator lights 290. The indicator lights 290 may be configured to indicate one or more of the following states: (a) that a sanitization cycle 1120 is underway, (b) that the sanitization cycle 1120 will soon be underway, (c) that the sanitization cycle 1120 is complete, (d) that the hubs 220 are active, (e) that the hubs 220 will soon be active, (f) that the hubs 220 are not active, (g) that there is some operational error, (h) that the hub system 200 is improperly configured on the MRI table 940, (i) that the sanitization cycle 1120 may have been ineffective in sanitizing the bore 920 and table 940 for one or more reasons, (j) that one or more proximity sensors 292 detects an person or some other obstruction, (k) that one or more proximity sensors 292 does not detect a bore 920, (l) that the surface temperature of the hubs 220 or hub system 220 exceeds a temperature threshold, or (m) some other state.

As described above, the sanitization operation 1100 includes a first step 1110 of translating the MRI table 940 into the MRI bore 920 and a second step of initiating a sanitization cycle 1120, which includes the activation of the hubs 220 of the hub system 200. When the hubs 220 are activated, the hubs 220 will radially emit a UV-C light that will reliably kill microbes, pathogens, and bacteria on the MRI bore surface 942, the MRI table 940, and within the MRI bore 920. As is well-established in the arts, UV-C light at a sufficiently high energy level will kill upwards of 99.9% of microbes, pathogens, and bacteria by inactivating the DNA or RNA of the microorganisms. For its efficacy in sanitization, UV-C light is used in a variety of healthcare applications.

Figure 10:
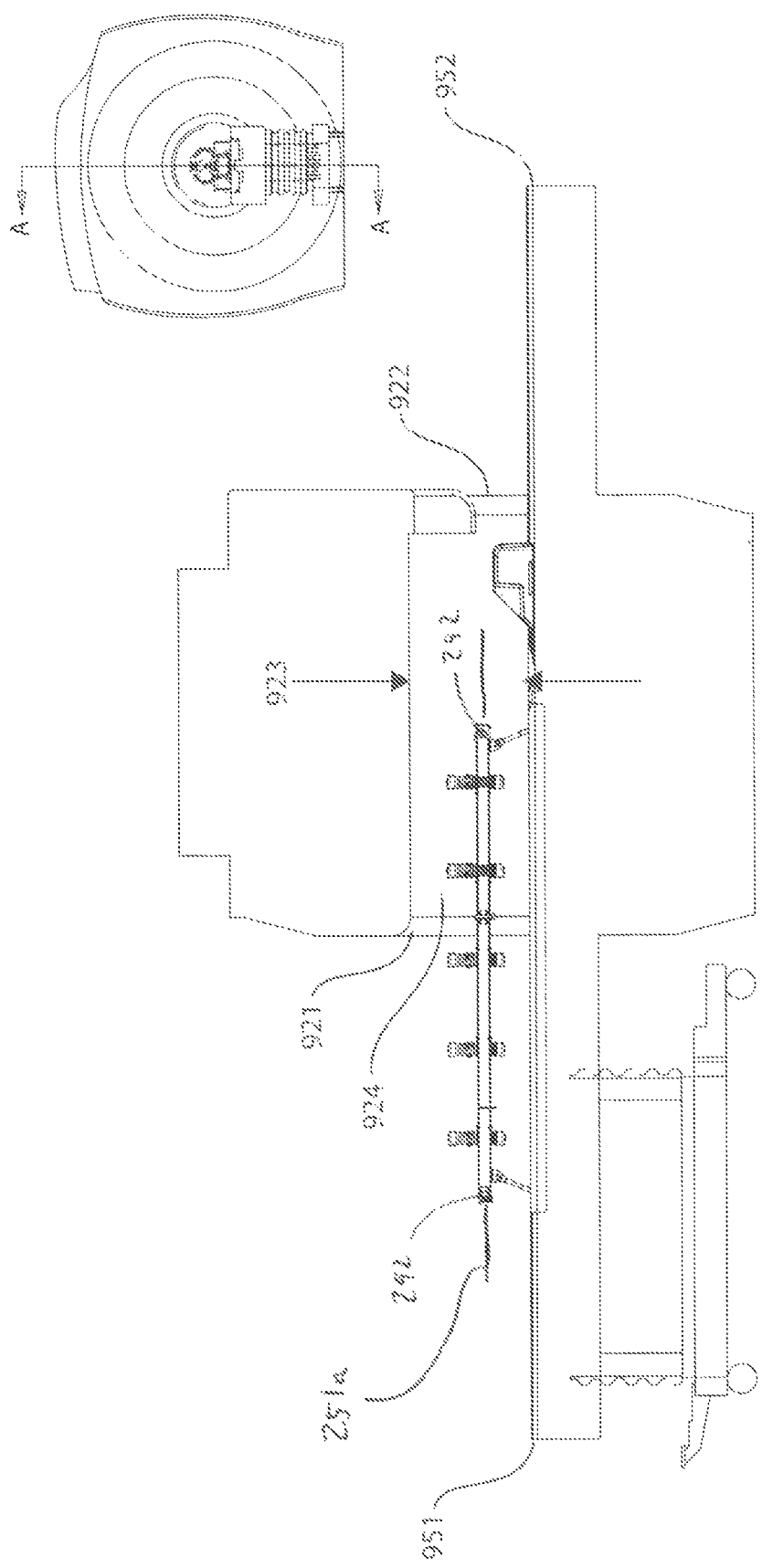
FIG. 10 is a right side elevation view of a hub system in a second position relative to an MRI machine, shown in partial cutaway.
Figure 11:
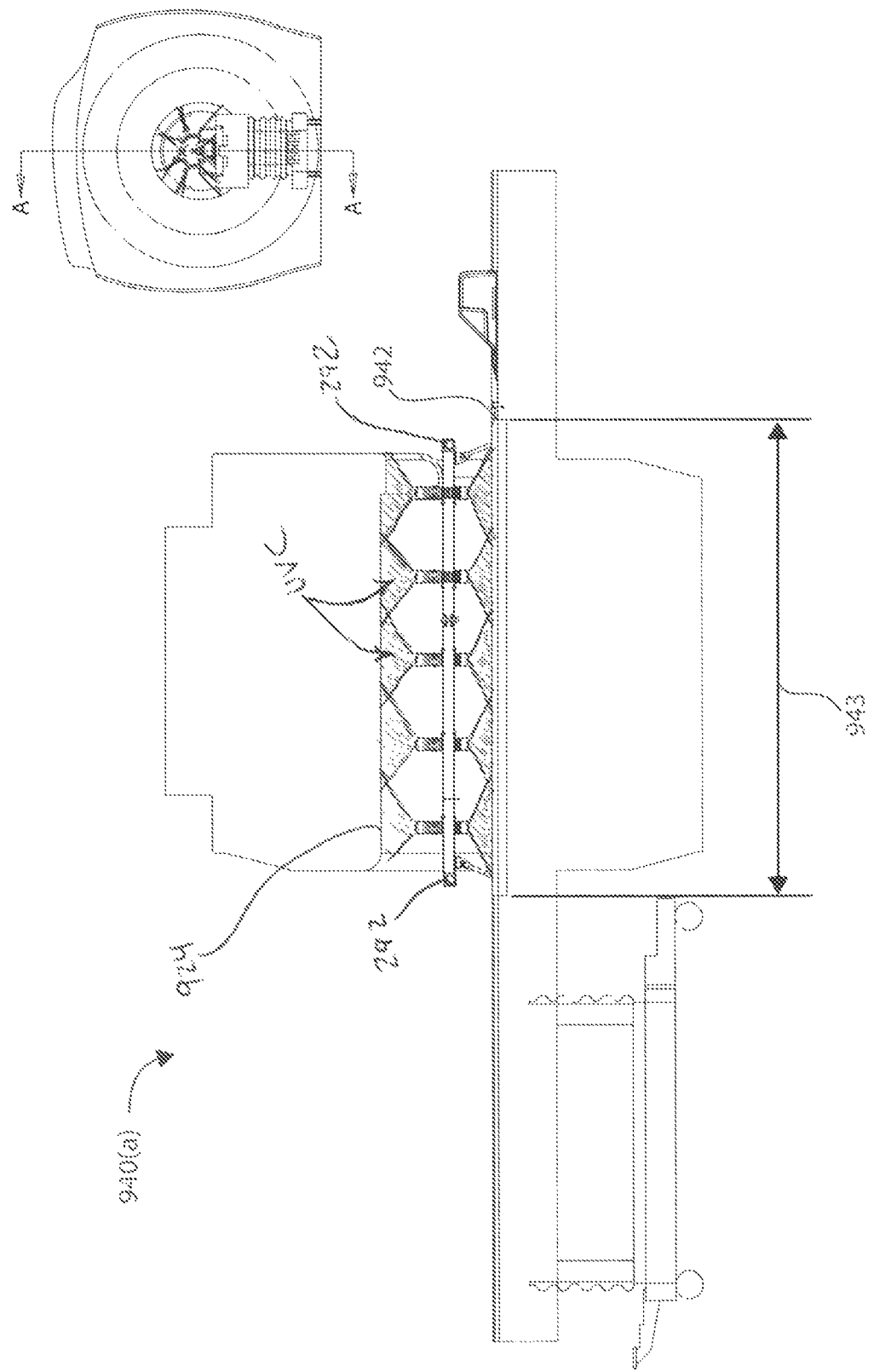
FIG. 11 is a right side elevation view of a hub system in a third position relative to an MRI machine, shown in partial cutaway.

As is also described above, each hub 220 is configured to radially emit UV-C light such that when the hub system 200 is atop the MRI table 940 and the table 940 is within the bore 920, the entire bore surface 924 and the entire table 940 are exposed to the UV-C light. As depicted in FIGS. 9-11, the hub system 200 is configured on the MRI table 940 by resting the legs 280 of the hub system 200 on the top surface 944 of the MRI table 940. In this position, each of the plurality of hubs 220 are elevated from the top surface 944 of the MRI table 940. Accordingly, the UV-C light emitted from each hub 220 will shine circumferentially outwardly onto a majority of the interior bore surface 924 and downward onto the top surface 944 of the MRI table 940, generally forming an at least substantially complete envelope of light on surfaces radially visible from the body 250. In preferred embodiments, as seen in FIG. 11, the light distribution of UV-C light UVC emitted from the hubs 220 will adequately cover the entire surface area of the MRI table surface 944 and the MRI bore surface 924 to ensure all microbes, pathogens, and bacteria are exposed to UV-C light.

Just as the hubs 220 are configured to distribute UV-C light radially so as to cover both the MRI bore surface 924 and the top surface 944 of the MRI table 940, the legs 280 may include a leg length 285 that optimizes the energy of the UV-C light exposure at the top surface 944 of the MRI table 940 and the MRI bore surface 924. Specifically, the leg length 285 is configured to position the hub system 200 on the MRI table 940 such that each hub 220 is an optimal distance above the MRI table 940 and in optimal proximity to the MRI bore surface 924 when the MRI table 940 is within the bore 920 in order to shine UV-C light of a sufficient light energy on to the MRI table top surface 944 and MRI bore surface 924. Specifically, the hub system 200 is configured to provide UV-C light at an energy of at least forty millijoules per centimeter squared (40 mJ/cm$^2$), which represents sufficient energy to kill all microbes, pathogens, and bacteria.

In other words, the positioning of the hub system 200 on the MRI table 940 and within the MRI bore 920, namely the position of the hubs 20 relative to the top surface 944 of the MRI table 940 and the MRI bore surface 924, must be sufficiently far from the MRI table top surface 944 and MRI bore surface 924 to realize sufficient light exposure, while simultaneously being sufficiently close to the MRI table top surface 924 and the MRI bore surface 924 to realize sufficient light energy.

Additionally, the duration of the sanitization cycle 1120 affects the efficacy of the UV-C light in killing microbes, pathogens, and bacteria. If the UV-C light is not distributed onto the bore surface 924 and table top surface 944, the hub system 200 may be ineffective in sanitizing. Therefore, it is necessary that the UV-C light be distributed for a sufficiently long period of time, such as five to seven (5-7) minutes or some other time interval.

Once sanitization cycle 1120 is complete, the controls panel 500 may be configured to automatically deactivate the hubs 220 or the user may need to manually command the hubs 220 to deactivate. Similarly, the hubs 220 may deactivate according to signals provided by proximity sensors 292 that, for example, detect that the MRI table 940 is being retracted from the bore 920. In any case, the hubs 220 are deactivated at the end of the sanitization cycle 1120.

Once the hubs 220 are deactivated (i.e. once the sanitization cycle 1120 is complete), a third and final step 1130 of the sanitization operation 1100 may be performed. The third step 1130 may include retracting the table 940 to its idle position 940(*b*).

After the three steps 1110, 1120, 1130 of the sanitization operation 1100 have been performed, the final dismantling procedure 1200 can be performed. The dismantling procedure includes a first step 1210, a second step 1220, a third step 1230, a fourth step 1240, and a fifth step 1250.

The first step 1210 may include transporting the cart 400 towards the MRI machine 900, specifically the MRI table 940 that has returned to the idle position 940(*b*) according to the third step 1130 of the sanitization operation 1100.

The second step 1220 of the dismantling procedure 1200 may require a user to disconnect the power cable 600 from the hub system 200. In particular, this may require a user to disconnect any jumper cables from jumper terminals in embodiments using a plurality of sub-body members 255 as well as disconnecting the power cable 600 from the power coupling point(s) on the hub system body 250. This step 1220 may result in an indicator light 290 turning off to indicate that power is no longer being delivered to the hub system 200.

The third step 1230 of the dismantling procedure 1200 may require the user to store the legs 280 of the hub system 200. Specifically, in embodiments including legs 280 rotatably mounted to the hub system body 250, the third step 1230 may require the user to rotate the legs 280 about the coupling aperture 283 into a position substantially parallel with the hub system body length 251.

The fourth step 1240 of the dismantling procedure 1200 includes storing the hub system 200 on the cart 400. This fourth step 1240 may also include a sub-step 1241 comprising the disassembly or folding of the hub system body 250 when the hub system body 250 comprises multiple sub-body members 255. For example, in an embodiment featuring a first and second sub-body member 260, 265, the sub-step 1241 may require the user to decouple the two sub-body members 260, 265 and store each on the cart 400.

The fifth and final step 1250 of the dismantling procedure 1200 may require the user to transport the cart 400 (which includes the stored hub system 200 and power cable 600) away from the MRI machine 900.

After the setup procedure 1000, sanitization operation 1100, and dismantling procedure 1200 have been completed, the imaging bore will be sanitized and prepared for the next scanning operation.

The foregoing is considered as illustrative only of the principles of the invention. Furthermore, because numerous modifications and changes will readily occur to those skilled in the art, it is not desired to limit the invention to the exact construction and operation shown and described. While the preferred embodiment has been described, the details may be changed without departing from the invention, which is defined by the claims.

What is claimed is:

1. A method comprising the steps of:
    placing a plurality of light-emitting devices into a hollow bore defined by an internal bore surface;
    in a first broadcasting step, broadcasting light from a first sub-plurality of the light-emitting devices onto a majority of the internal bore surface; and
    positioning a longitudinal body substantially parallel to a table, the table being translatable into and out of the hollow bore,
    wherein the plurality of light-emitting devices are mounted to a plurality of hubs spaced along the longitudinal body.

2. A method according to claim 1, further comprising the step of:
    positioning the hubs between the table and the bore surface, the hubs being spaced from the table.

3. A method according to claim 2, further comprising the step of:
    in a second broadcasting step, broadcasting light from a second sub-plurality of light-emitting devices onto a majority of a top surface of the table.

4. A method according to claim 3, further comprising the step of:
    as a result of the first and second broadcasting steps, reducing a viable concentration of at least one of microbes, pathogens, and bacteria on the bore surface and on the top surface of the table.

5. A method according to claim 3, wherein the first broadcasting step and the second broadcasting step are performed at least substantially simultaneously.

6. A method according to claim 5, wherein the first broadcasting step causes the majority of the bore surface to receive a light energy density of about 20 millijoules per centimeter squared (mJ/cm2) to about 50 mJ/cm2, and
    wherein the second broadcasting step causes the majority of the top surface of the table to receive a light energy density of about 20 mJ/cm2 to about 50 mJ/cm2.

* * * * *